United States Patent
Choi et al.

(10) Patent No.: US 11,510,899 B2
(45) Date of Patent: Nov. 29, 2022

(54) RTX TOXIN PRODUCTION INHIBITOR AND COMPOSITION FOR TREATING SYMPTOM OF VIBRIO INFECTION BY USING SAME

(71) Applicant: SEOUL NATIONAL UNIVERSITY R&DB FOUNDATION, Seoul (KR)

(72) Inventors: Sang Ho Choi, Seoul (KR); Lak Shin Jeong, Seoul (KR); Ho Jae Han, Seoul (KR); Nam Chul Ha, Seoul (KR); Byoung Sik Kim, Yongin-si (KR); Kyung Ku Jang, Seoul (KR); Zee-Won Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 115 days.

(21) Appl. No.: 16/637,053

(22) PCT Filed: Jan. 7, 2019

(86) PCT No.: PCT/KR2019/000218
§ 371 (c)(1),
(2) Date: Feb. 6, 2020

(87) PCT Pub. No.: WO2019/151664
PCT Pub. Date: Aug. 8, 2019

(65) Prior Publication Data
US 2020/0237718 A1    Jul. 30, 2020

(30) Foreign Application Priority Data

Jan. 31, 2018  (KR) .......................... 10-2018-0012353
Nov. 14, 2018  (KR) .......................... 10-2018-0139927

(51) Int. Cl.
*A61P 31/04* (2006.01)
*A61K 31/382* (2006.01)

(52) U.S. Cl.
CPC ............ *A61K 31/382* (2013.01); *A61P 31/04* (2018.01)

(58) Field of Classification Search
CPC ....... A61K 31/382; A61K 31/03; A61P 31/04; C07D 495/04
See application file for complete search history.

(56) References Cited

U.S. PATENT DOCUMENTS 9,222,118 B2 * 12/2015 Kawaoka ............... A61K 31/05

FOREIGN PATENT DOCUMENTS

| KR | 10-0515767 B1 | 9/2005 |
| KR | 10-1613347 B1 | 4/2016 |
| WO | 2011/103189 A1 | 8/2011 |

OTHER PUBLICATIONS

Registry No. 588678-13-1, Chemical Abstract Service STN Database [online][Entered STN: Sep. 19, 2003], (Year: 2003).*
Registry No. 866735-60-6, Chemical Abstract Service STN Database [online][Entered STN: Nov. 4, 2005]. (Year: 2005).*
Fullner et al., "Genetic Characterization of a New Type IV-A Pilus Gene Cluster Found in Both Classical and El Tor Biotypes of Vibrio cholerae", Infect. Immun., 1999, vol. 67, No. 3, pp. 1393-1404.
Guzman et al., "Tight Regulation, Modulation, and High-Level Expression by Vectors Containing the Arabinose PBAD Promoter", J. Bacteriol., 1995, vol. 177, No. 14, pp. 4121-4130.
Jang et al. "Identification and characterization of Vibrio vulnificus plpA encoding a phospholipase A2 essential for pathogenesis", J. Biol. Chem., 2017, vol. 292, No. 41, pp. 17129-17143.
Lenz et al., "The Small RNA Chaperone Hfq and Multiple Small RNAs Control Quorum Sensing in Vibrio harveyi and Vibrio cholerae", Cell, 2004, vol. 118, pp. 69-82.
Al-Zaydi et al., "Studies with heteroaromatic amines. A new route to 2-azolylamino-2-thiazolin-4-ones.", Journal of Chemical Research, 2006, vol. 6, pp. 408-411.
Al-Zaydi et al., "Functionally substituted 1-alkylbenzotriazoles in Heterocyclic synthesis: Synthesis and Reactivity of Benzotriazol-1-yl amides", 2013, 8 pages.
Fondjo et al., "Synthesis, Characterization, Antimicrobial and Antioxidant Activities of The Homocyclotrimer of 4-Oxo-4h-Thieno[3,4-C]Chromene-3-Diazonium Sulfate", The Open Medicinal Chemistry Journal, 2016, vol. 10, pp. 21-32.
Tamokou et al., "Antibacterial and Cytotoxic Activities and SAR of Some Azo Compounds Containing Thiophene Backbone", Pharmacologia, 2016, vol. 7, No. 4, pp. 182-192.

* cited by examiner

*Primary Examiner* — Amanda L. Aguirre
(74) *Attorney, Agent, or Firm* — Vorys, Sater, Seymour & Pease LLP; Mih Suhn Koh

(57) ABSTRACT

Provided is a method for treating a symptom of vibrio infection by using an RTX toxin production inhibitor comprising N-(4-oxo-4H-thieno[3,4-c]chromen-3-yl)-3-phenylprop-2-ynamide having derivatives thereof which can repress (prevent or treat) a symptom of vibrio infection by inhibiting RTX toxin production, other than directly killing vibrio bacteria, to not allow vibrio bacteria to have pathogenicity, and thereby can be an alternative to antibiotics that aim to kill bacteria themselves and thus fundamentally retain the problem of resistance incurrence.

3 Claims, 29 Drawing Sheets
(17 of 29 Drawing Sheet(s) Filed in Color)

FIG. 26

RTX TOXIN PRODUCTION INHIBITOR AND COMPOSITION FOR TREATING SYMPTOM OF VIBRIO INFECTION BY USING SAME

TECHNICAL FIELD

The present invention relates to an RTX toxin production inhibitor and a composition for treating *Vibrio* infection using the same.

BACKGROUND ART 34 species of *Vibrio* have been discovered to date, and the cells thereof are not long but bent, and are dependently singular or are connected in a spiral form. One end of the body has one or more flagella, which are used to actively swim and move. *Vibrio* is a gram-negative bacterium, and wild species thereof are widely distributed in the sea and are also found in fresh water and soil.

There are *Vibrio* species exhibiting pathogenic effects in humans, fish and shellfish, and typical pathogenic *Vibrio* species include *Vibrio* cholerae, *Vibrio* parahaemolyticus, *Vibrio* vulnificus and *Vibrio* alginolyticus.

*Vibrio* cholera (*V. cholerae*) is a bacterium that causes cholera, well-known for infectious diarrhea. Cholera infection is known to cause incessant runny diarrhea of the form of rice water, leading to death from dehydration without proper fluid replenishment. *V. cholerae* is highly infectious enough to be classified as a first-class legal epidemic pathogen in Korea.

*Vibrio parahaemolyticus* (*V. parahaemolyticus*) lives mainly in seawater and may thus be contracted due to the digestion of raw or undercooked seafood, which is also called "enteritis vibrio" because it causes enteritis.

*Vibrio vulnificus* (*V. vulnificus*) lives primarily in seawater and grows well in summer. When patients having reduced immunity due to various chronic diseases eat raw or undercooked seafood, they may suffer from serious sepsis such as high fever and reduction in blood pressure as well as severe infection of the arms and legs.

*Vibrio alginolyticus* (*V. alginolyticus*) is present in the body of marine organisms such as blowfish and produces tetrodotoxin, which is an intraperitoneal toxin, mainly causing otitis and wound infections.

Meanwhile, pathogenic microorganisms survive and proliferate in hosts through the production of various virulence factors that are virulent to the hosts, and develop regulatory mechanisms by which the various virulence factors are collectively expressed and act during the onset thereof. The regulatory mechanisms of these virulence factors are considerably sophisticated and the production of the virulence factors can be suppressed by inhibiting the regulatory mechanisms. This can reduce the virulence of the pathogenic microorganisms and easily inhibit the virulence of the microorganisms through the host's immune response.

Inhibition of the mechanism of production of virulence factors is unlikely to cause antibiotic resistance because the growth of microorganisms is not artificially inhibited, and is thus attracting a lot of attention as a new pathogenic microbial treatment strategy. However, studies that have been actively conducted to date have been limited to specific microorganisms, and studies on inhibition of virulence factor production regulatory mechanisms for other pathogenic microorganisms are unsatisfactory.

DISCLOSURE

Technical Problem

Therefore, the present invention has been made in view of the above problems, and it is one object of the present invention to develop and provide a substance for treating an infection or disease caused by *Vibrio* bacteria that is capable of removing pathogenicity of *Vibrio* bacteria by inhibiting the production of RTX toxins rather than killing *Vibrio* bacteria.

Technical Solution

In accordance with an aspect of the present invention, the above and other objects can be accomplished by the provision of a pharmaceutical composition for preventing or treating *Vibrio* infection containing N-(4-oxo-4H-thieno[3,4-c]chromen-3-yl)-3-phenylprop-2-ynamide having the structure of the following Formula 11 or a derivative thereof, wherein the derivative includes any one selected from a compound having the structure of the following Formula 12, a compound having the structure of the following Formula 13, a compound having the structure of the following Formula 14, a compound having the structure of the following Formula 15, a compound having the structure of the following Formula 16, and a compound having the structure of the following Formula 17:

[Formula 11]

[Formula 12]

[Formula 13]

[Formula 14]

[Formula 15]

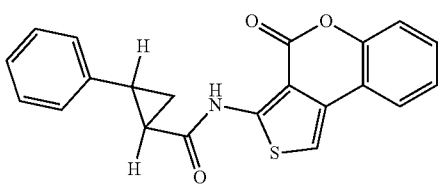

[Formula 16]

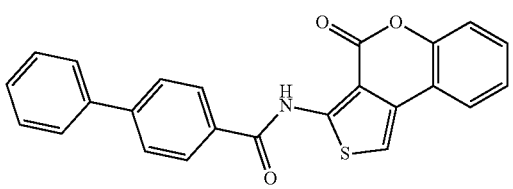

[Formula 17]

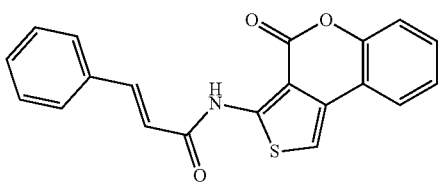

In accordance with another aspect of the present invention, provided is a pharmaceutical composition for preventing or treating *Vibrio* infection containing N-(4-oxo-4H-thieno[3,4-c]chromen-3-yl)-3-phenylprop-2-ynamide having the structure of the following Formula 11 or a derivative thereof, wherein the derivative includes any one selected from a compound having the structure of the following Formula 21, a compound having the structure of the following Formula 22, a compound having the structure of the following Formula 23, a compound having the structure of the following Formula 24, a compound having the structure of the following Formula 25, a compound having the structure of the following Formula 26, a compound having the structure of the following Formula 27, a compound having the structure of the following Formula 28 and a compound having the structure of the following Formula 29:

[Formula 11]

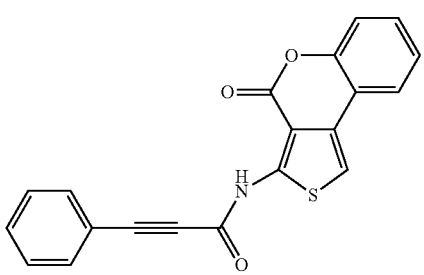

[Formula 21]

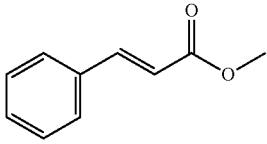

[Formula 22]

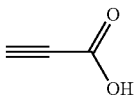

[Formula 23]

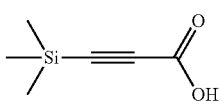

[Formula 24]

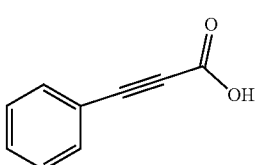

[Formula 25]

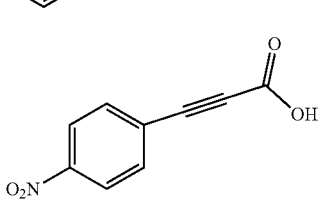

[Formula 26]

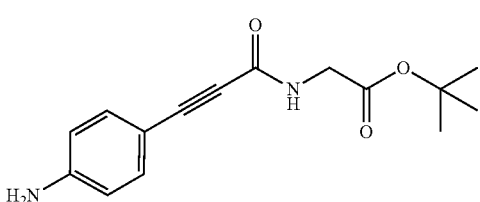

[Formula 27]

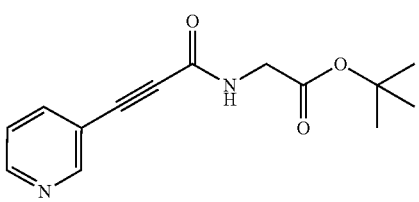

[Formula 28]

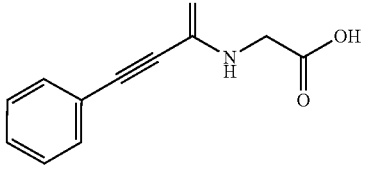

[Formula 29]

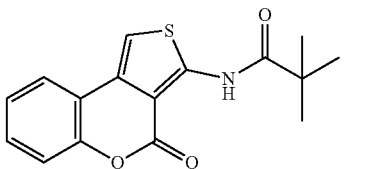

In the pharmaceutical composition for preventing or treating *Vibrio* infection of the present invention, the N-(4-oxo-4H-thieno[3,4-c]chromen-3-yl)-3-phenylprop-2-ynamide or a derivative thereof preferably inhibits the activity of HlyU by covalently binding to the transcriptional regulator protein, HlyU, which activates the expression of rtxA, which is an RTX toxin gene of *Vibrio* bacteria, vvhA, which is a hemolysin gene thereof, and plpA, which is a phospholipase gene thereof.

In the pharmaceutical composition for preventing or treating Vibrio infection of the present invention, the Vibrio bacteria may be, for example, any one selected from Vibrio cholerae, Vibrio parahaemolyticus, Vibrio vulnificus and Vibrio alginolyticus.

In accordance with another aspect of the present invention, provided is a food composition for alleviating Vibrio infection containing N-(4-oxo-4H-thieno[3,4-c]chromen-3-yl)-3-phenylprop-2-ynamide having the structure of Formula 11 or a derivative thereof, wherein the derivative includes any one selected from the compound having the structure of Formula 12, the compound having the structure of the following Formula 13, the compound having the structure of Formula 14, the compound having the structure of Formula 15, the compound having the structure of Formula 16, and the compound having the structure of Formula 17.

In accordance with another aspect of the present invention, provided is a food composition for alleviating Vibrio infection containing N-(4-oxo-4H-thieno[3,4-c]chromen-3-yl)-3-phenylprop-2-ynamide having the structure of Formula 11 or a derivative thereof, wherein the derivative includes any one selected from the compound having the structure of Formula 21, the compound having the structure of Formula 22, the compound having the structure of Formula 23, the compound having the structure of Formula 24, the compound having the structure of Formula 25, the compound having the structure of Formula 26, the compound having the structure of Formula 27, the compound having the structure of Formula 28 and the compound having the structure of Formula 29.

In the food composition for alleviating Vibrio infection of the present invention, the N-(4-oxo-4H-thieno[3,4-c]chromen-3-yl)-3-phenylprop-2-ynamide or a derivative thereof preferably inhibits the activity of HlyU by covalently binding to the transcriptional regulator protein, HlyU, which activates the expression of rtxA, which is an RTX toxin gene of Vibrio bacteria, vvhA, which is a hemolysin gene thereof, and plpA, which is a phospholipase gene thereof.

In the food composition for alleviating Vibrio infection of the present invention, the Vibrio bacteria may be, for example, any one selected from Vibrio cholerae, Vibrio parahaemolyticus, Vibrio vulnificus and Vibrio alginolyticus.

Advantageous Effects

The N-(4-oxo-4H-thieno[3,4-c]chromen-3-yl)-3-phenylprop-2-ynamide having a structure of Formula 11 or a derivative thereof developed according to the present invention, that is, the compound having the structure of Formula 12, the compound having the structure of Formula 13, the compound having the structure of Formula 14, the compound having the structure of Formula 15, the compound having the structure of Formula 16, the compound having the structure of Formula 17, the compound having the structure of Formula 21, the compound having the structure of Formula 22, the compound having the structure of Formula 23, the compound having the structure of Formula 24, the compound having the structure of Formula 25, the compound having the structure of Formula 26, the compound having the structure of Formula 27, the compound having the structure of Formula 28 or the compound having the structure of Formula 29 is capable of inhibiting (preventing or treating) Vibrio infection by removing pathogenicity of Vibrio bacteria by inhibiting the production of RTX toxins rather than killing Vibrio bacteria. Accordingly, the present invention can be an alternative to antibiotics that inherently target killing of bacteria and thus have the problem of causing resistance.

BRIEF DESCRIPTION OF DRAWINGS

The patent or application file contains at least one drawing executed in color. Copies of this patent or patent application publication with color drawing(s) will be provided by the Office upon request and payment of the necessary fee.

The hlyU (strain) shown in the drawings of the present invention represents a mutant strain in which the hlyU gene is knocked out. In addition, CM2660 shown in the drawing is N-(4-oxo-4H-thieno[3,4-c]chromen-3-yl)-3-phenylprop-2-ynamide having the chemical structural represented by Formula 11.

Figure 26:
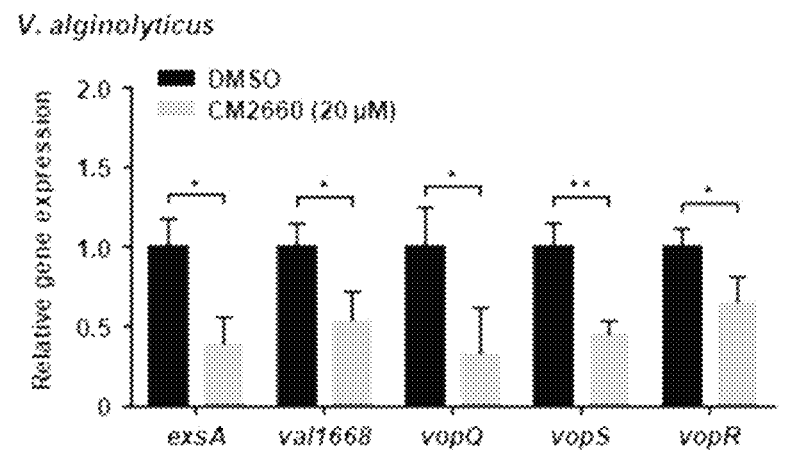

FIG. 26 shows the results of determination of mRNA levels of exsA, va11668, vopQ, vopS and vopR at $A_{600}=0.5$ when treating *Vibrio alginolyticus* with 20 µM CM2660;

BEST MODE

Figure 1:
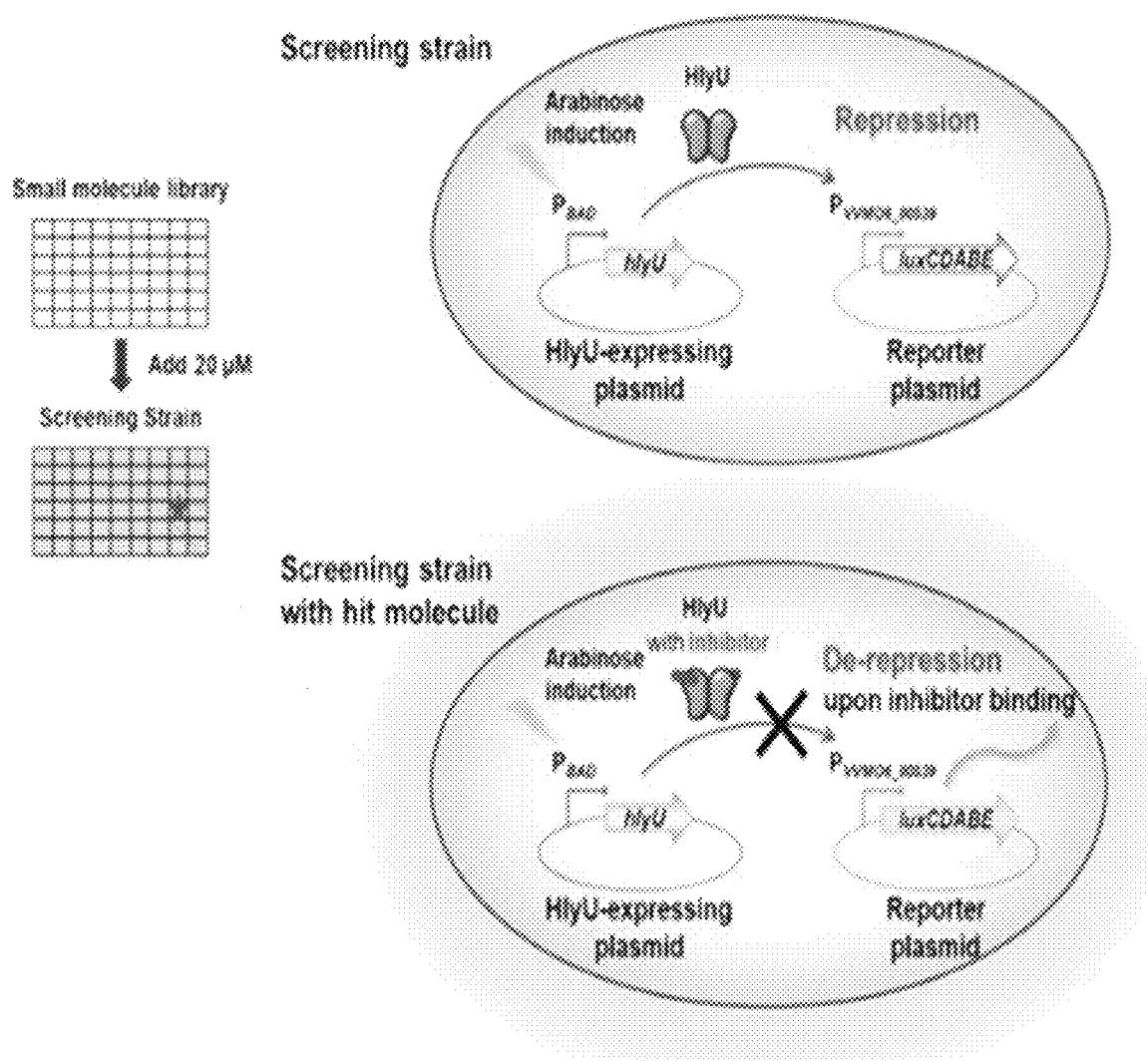
FIG. 1 is a schematic diagram illustrating the strategy used to screen selective inhibitors of HlyU.

The present invention provides a pharmaceutical composition for preventing or treating *Vibrio* infection containing N-(4-oxo-4H-thieno[3,4-c]chromen-3-yl)-3-phenylprop-2-ynamide having the structure of the following Formula 11 or a derivative thereof, wherein the derivative includes any one selected from a compound having the structure of the following Formula 12, a compound having the structure of the following Formula 13, a compound having the structure of the following Formula 14, a compound having the structure of the following Formula 15, a compound having the structure of the following Formula 16, and a compound having the structure of the following Formula 17.

The compound having the structure of Formula 11 to the compound having the structure of Formula 17 according to the present invention include the structure of Formula 10 below in common, and may be also referred to as "Compound I Group" below.

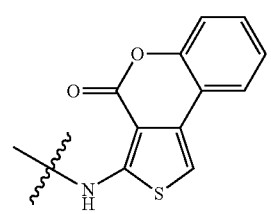

[Formula 10]

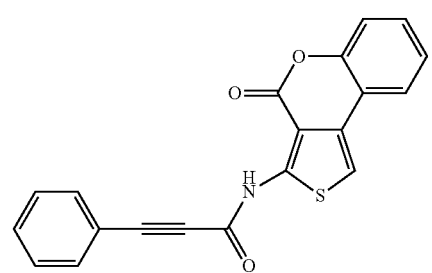

[Formula 12]

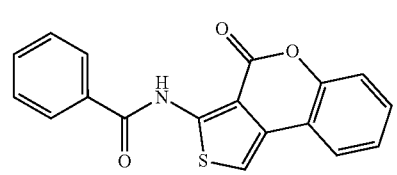

[Formula 12]

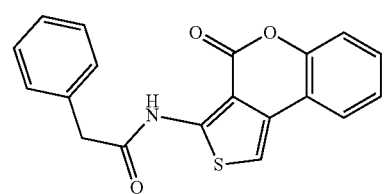

[Formula 13]

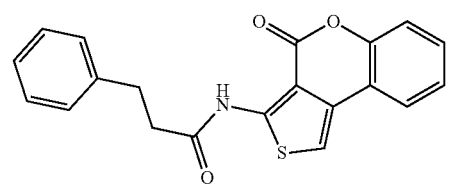

[Formula 14]

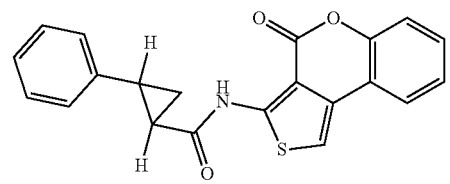

[Formula 15]

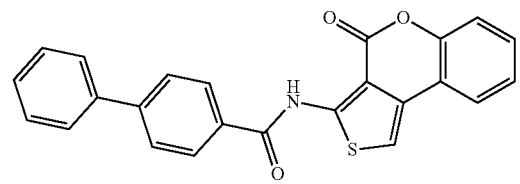

[Formula 16]

[Formula 17]

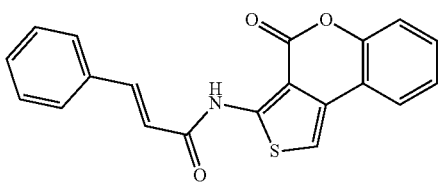

The present invention provides a pharmaceutical composition for preventing or treating *Vibrio* infection containing N-(4-oxo-4H-thieno[3,4-c]chromen-3-yl)-3-phenylprop-2-ynamide having the structure of the following Formula 11 or a derivative thereof, wherein the derivative includes any one selected from a compound having the structure of the following Formula 21, a compound having the structure of the following Formula 22, a compound having the structure of the following Formula 23, a compound having the structure of the following Formula 24, a compound having the structure of the following Formula 25, a compound having the structure of the following Formula 26, a compound having the structure of the following Formula 27, a compound having the structure of the following Formula 28 and a compound having the structure of the following Formula 29.

The compound having the structure of Formula 11 and the compound having the structure of Formula 21 to the compound having the structure of Formula 29 according to the present invention include the structure of Formula below in common, and may be also referred to as "Compound II Group" below.

[Formula 20]

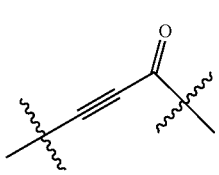

[Formula 11]

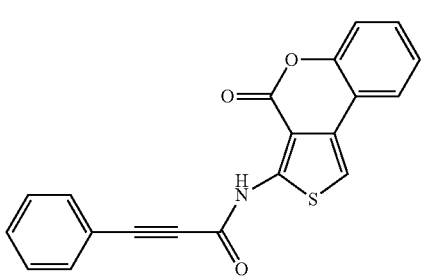

[Formula 21]

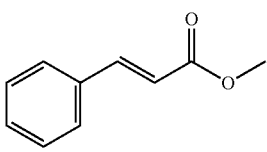

[Formula 22]

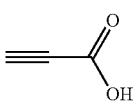

[Formula 23]

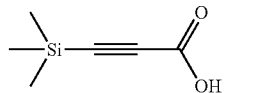

[Formula 24]

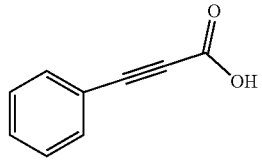

[Formula 25]

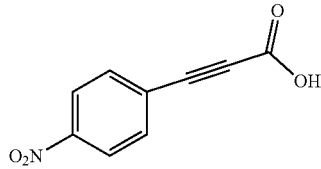

[Formula 26]

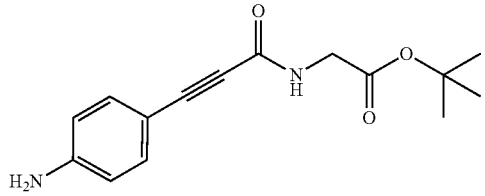

[Formula 27]

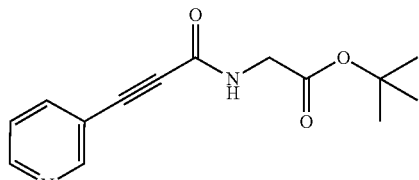

[Formula 28]

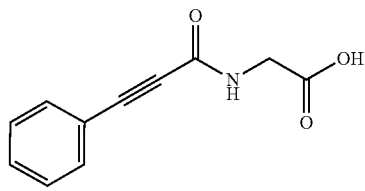

[Formula 29]

The N-(4-oxo-4H-thieno[3,4-c]chromen-3-yl)-3-phenyl-prop-2-ynamide or a derivative thereof preferably inhibits the activity of HlyU by covalently binding to the transcriptional regulator protein, HlyU, which activates the expression of rtxA, which is an RTX toxin gene of *Vibrio* bacteria, vvhA, which is a hemolysin gene thereof, and plpA, which is a phospholipase gene thereof. The *Vibrio* bacteria may be, for example, any one selected from *Vibrio* cholerae, *Vibrio* parahaemolyticus, *Vibrio* vulnificus, and *Vibrio* alginolyticus.

*V. vulnificus* is known to produce various virulence factors such as capsular polysaccharide, lipopolysaccharide, RTX toxins (RtxA), hemolysin (VvhA), phospholipase $A_2$ (PlpA) and adhesion proteins, thus causing disease. Among them, the expression of each of the major virulence factors, RtxA, VvhA and PlpA genes is known to be activated by the transcriptional regulator, HlyU.

The present invention aims to identify that the N-(4-oxo-4H-thieno[3,4-c]chromen-3-yl)-3-phenylprop-2-ynamide or a derivative thereof inhibits HlyU proteins, and develop and provide the same as a composition for preventing or treating Vibrio-induced sepsis. That is, the N-(4-oxo-4H-thieno[3,4-c]chromen-3-yl)-3-phenylprop-2-ynamide (CM2660, Formula 11) or derivatives thereof, that is, LJ4451 (Formula 12), LJ4457 (Formula 13), LJ4458 (Formula 14), LJ4459 (Formula 15), LJ4460 (Formula 16), LJ4461 (Formula 17), LJ4522 (Formula 21), LJ4523 (Formula 22), LJ4524 (Formula 23), LJ4525 (Formula 24), LJ4526 (Formula 25), LJ4531 (Formula 26), LJ4532 (Formula 27), LJ4533 (Formula 28) and LJ4534 (Formula 29), can be used as an RtxA toxin production inhibitor that prevents binding to the target DNA associated with toxicity by covalently binding with the HlyU protein.

The present invention aims to prevent or treat diseases caused by Vibrio infection by lowering or removing the virulence of Vibrio bacteria by inhibiting HlyU protein associated with expression of virulence factors, rather than directly killing Vibrio bacteria. For this reason, the present invention has the advantage of being free from problems such as resistance caused by the use of antibiotics.

Meanwhile, the pharmaceutical composition for preventing or treating Vibrio infection of the present invention may further contain a pharmaceutically acceptable carrier, diluent or excipient, in addition to the active ingredient. The carrier, excipient or diluent which may be used in the present invention includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrolidone, water, methylhydroxybenzoate, propylhydroxybenzoate, talc, magnesium stearate and mineral oil, and one or more selected from these substances may be used. In addition, the pharmaceutical composition for preventing or treating Vibrio infection of the present invention may further contain one or more selected from fillers, anticoagulants, lubricants, wetting agents, fragrances, emulsifiers and preservatives.

Meanwhile, the formulation of the pharmaceutical composition for preventing or treating Vibrio infection of the present invention may be a preferred form depending on the method of use, and in particular, the pharmaceutical composition is preferably formulated by adopting a method well-known in the art to provide rapid, sustained or delayed release of the active ingredient after administration to a mammal. Specific examples of the formulation include any one selected from plasters, granules, lotions, liniments, limonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, ETS, spirits, cataplasms, capsules, creams, troches, tinctures, pastes, pills, and soft or hard gelatin capsules.

Meanwhile, the dosage of the pharmaceutical composition for preventing or treating Vibrio infection of the present invention is preferably determined in consideration of factors such as the method of administration, the age, gender and weight of the subject, and severity of the disease. For example, the pharmaceutical composition for preventing or treating Vibrio infection of the present invention may be administered at least once daily at 0.00001 to 100 mg/kg (body weight), based on the active ingredient. However, this dosage is provided only as an example for illustration, and may be changed according to a physician's prescription depending on the condition of the subject.

Meanwhile, the present invention provides a food composition for alleviating Vibrio infection containing N-(4-oxo-4H-thieno[3,4-c]chromen-3-yl)-3-phenylprop-2-ynamide having the structure of Formula 11 or a derivative thereof, wherein the derivative includes any one selected from the compound having the structure of Formula 12, the compound having the structure of the following Formula 13, the compound having the structure of Formula 14, the compound having the structure of Formula 15, the compound having the structure of Formula 16, and the compound having the structure of Formula 17.

Also, the present invention provides a food composition for alleviating Vibrio infection containing N-(4-oxo-4H-thieno[3,4-c]chromen-3-yl)-3-phenylprop-2-ynamide having the structure of Formula 11 or a derivative thereof, wherein the derivative includes any one selected from the compound having the structure of Formula 21, the compound having the structure of Formula 22, the compound having the structure of Formula 23, the compound having the structure of Formula 24, the compound having the structure of Formula 25, the compound having the structure of Formula 26, the compound having the structure of Formula 27, the compound having the structure of Formula 28 and the compound having the structure of Formula 29.

In the food composition for alleviating Vibrio infection of the present invention, the N-(4-oxo-4H-thieno[3,4-c]chromen-3-yl)-3-phenylprop-2-ynamide (CM2660) or a derivative thereof is preferably present in an amount of 0.00001 to 50% by weight with respect to the food composition for alleviating Vibrio infection. When the N-(4-oxo-4H-thieno[3,4-c]chromen-3-yl)-3-phenylprop-2-ynamide (CM2660) or a derivative thereof is present in an amount less than 0.00001% by weight, the effect is insignificant, and when it exceeds 50% by weight, the increase in effect compared to the amount of use is uneconomically unsatisfactory.

The food composition for alleviating Vibrio infection of the present invention includes, for example, any one selected from meat, cereals, caffeinated beverages, general beverages, chocolate, bread, snacks, confectioneries, candy, pizza, jellies, noodles, gum, dairy products, ice cream, alcoholic beverages, liquors, vitamin complexes and other health supplements, but is not necessarily limited thereto.

Mode for Invention

Hereinafter, the present invention will be described in more detail with reference to the following Examples or Experimental Examples. However, the scope of the present invention is not limited to these Examples or Experimental Examples and also includes modifications equivalent thereto.

EXAMPLE 1

High-Throughput Screening for Selection of HlyU Inhibitor

The bacterial species and plasmids used in this experiment are summarized in Table 1.

TABLE 1

| Strains or plasmids | Relevant characteristics [a] | Reference or source |
|---|---|---|
| Bacterial strains | | |
| *V. vulnificus* | | |
| MO6-24/O | Clinical isolate, virulent | From laboratory of present inventor, Professor Sang Ho Choi |
| ZW141 | MO6-24/O with ΔhlyU | Reference 1 |
| *V. parahaemolyticus* | | |
| FORC_008 | Clinical isolate, virulent | From laboratory of present inventor, Professor Sang Ho Choi |
| *V. alginolyticus* | | |
| ATCC17749 | virulent | Korean Collection for Type Cultures |
| *V. cholerae* | | |
| El Tor N16961 | Clinical isolate, virulent | Reference 2 |
| *E. coli* | | |
| DH5α | supE44 ΔlacU169 (Φ80 lacZ ΔM15) hsdR17 recA1 endA1 gyrA96 thi-1 relAI | From laboratory of present inventor, Professor Sang Ho Choi |
| Plasmids | | |
| pBBR_lux | Broad host range vector within promoterless luxCDABE; $Cm^r$ | Reference 3 |
| pZW1608 | pBBR_lux with $P_{VVMO6\_00539}$, $Cm^r$ | Present invention |
| pKK1305 | pBBR_lux with $P_{rtxA}$, $Cm^r$ | Present invention |
| pBAD24 | Expression vector with the $P_{BAD}$ promoter; $Ap^r$ | Reference 4 |
| pKK1306 | pBAD24 with hlyU; $Ap^r$ | Present invention |

[a] $Ap^r$, ampicillin-resistant; $Cm^r$, chloramphenicol-resistant.

The *Escherichia coli* used in the present invention was cultured at 37° C. in Luria-Bertani (LB) medium. *V. vulnificus* was cultured at a temperature of 30° C. in LB medium (LBS) supplemented with 2% NaCl. If necessary, 100 μg/ml of ampicillin was used for *E. coli* and *Vibrio vulnificus*, and 20 μg/ml and 3 μg/ml of chloramphenicol were used for *E. coli* and *Vibrio vulnificus*, respectively.

Meanwhile, to perform *E. coli* reporter strain construction and high-throughput screening, a pKK1306 plasmid cloned to induce wild-type hlyU genes by arabinose was constructed. The reporter plasmid is pZW1608, in which the promoter of the VVMO6_00539 gene, expression of which is directly repressed by HlyU, is cloned in front of the bioluminescence operon (lux operon). These two plasmids were simultaneously transformed into *E. coli* DH5 to construct an *E. coli* reporter strain (FIG. 1). FIG. 1 is a schematic diagram illustrating the strategy used to screen selective inhibitors of HlyU. The *E. coli* reporter strain was found to decrease bioluminescence with increasing arabinose concentration, and was used as a reporter system to screen HlyU inhibitors.

For the screening, approximately 8400 low-molecular-weight compounds were obtained from Korea Compound Bank and used in this experiment. *Escherichia coli* reporter strains cultured for 16 hours were inoculated in a 100-fold dilution in LB medium, and arabinose was added to a final concentration of 0.0002%. In the positive control group, HlyU was prevented from being expressed by adding water instead of arabinose so that lux operon expression of the reporter plasmid was not inhibited. When the absorbance at 600 nm ($A_{600}$) of the culture solution, which was cultured at 37° C., reached 0.5, 100 μl of the culture solution was transferred to a 96-well black plate. Each well was treated at a final concentration of 20 μM with the respective compounds and dimethyl sulfoxide (DMSO) as a control group. While culturing at 37° C., the growth and bioluminescence of the reporter strain were measured using an Infinite™ M200 microplate reader (Tecan, Mannedorf, Switzerland). The relative luminescence unit (RLU) was calculated through normalization by division of the measured luminescence value by the absorbance.

$$RLU = luminescence/absorbance \quad \text{[Equation 1]}$$

The activity of about 8,400 compounds was screened using the *E. coli* reporter strain. As a result, some compounds inhibited the growth of *E. coli*, while others increased bioluminescence without affecting the growth of bacteria. A total of seven compounds (1025E12, 1030B04, 1040E12, 855B03, 855D03, 855F03 and 855G03) were screened as candidate inhibitors of HlyU, and these compounds significantly increased the bioluminescence of *E. coli* reporter strains.

Figure 2:
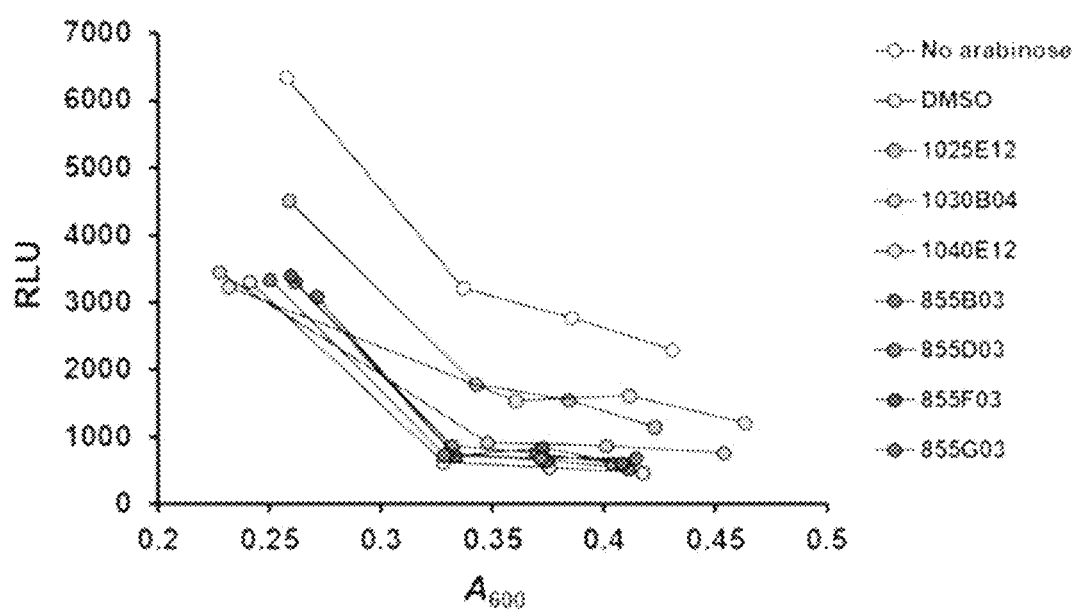
FIG. 2 shows the result of verification of the HlyU inhibitory activity of 1025E12 (hereinafter referred to as "CM2660"), 1030B04, 1040E12, 855B03, 855D03, 855F03 and 855G03 using E. coli screening strains.

The seven compounds (1025E12, 1030B04, 1040E12, 855B03, 855D03, 855F03 and 855G03) were transferred to fresh plates and were subjected to experimentation again using *E. coli* reporter strains to verify the results of the high-throughput screening. In this verification experiment, the cells were cultured for 4 hours, and the growth and bioluminescence of *E. coli* were measured every hour (FIG. 2). FIG. 2 shows the result of verification of the HlyU inhibitory activity of 1025E12 (hereinafter referred to as "CM2660"), 1030B04, 1040E12, 855B03, 855D03, 855F03 and 855G03 using *E. coli* screening strains.

Meanwhile, verification experiments using the *Vibrio* reporter strain were also conducted so as to exclude false positive results. It was identified that the effect of the compound was not limited only to *E. coli* using *Vibrio vulnificus*, each having the reporter plasmid (pZW1608) inhibited by HlyU, which was used for the *E. coli* reporter strain, and the plasmid (pKK1305) in which the promoter of the rtxA gene activated by HlyU is cloned in front of the bioluminescence operon.

Figure 3:
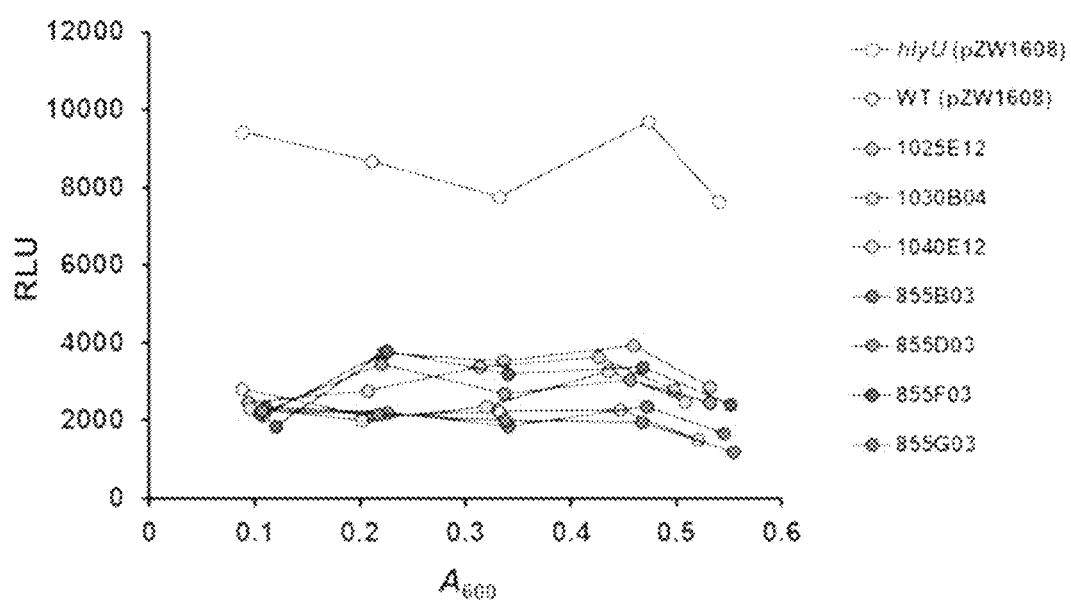
FIG. 3 shows the results of verification of HlyU inhibitory activity of 1025E12 (hereinafter referred to as "CM2660"), 1030B04, 1040E12, 855B03, 855D03, 855F03 and 855G03 using wild-type Vibrio vulnificus introduced with the lux reporter plasmid (pZW1608), lux expression of which is repressed by HlyU, and hlyU-mutant Vibrio vulnificus introduced with the lux reporter plasmid (pZW1608), lux expression of which is repressed by HlyU.
Figure 4:
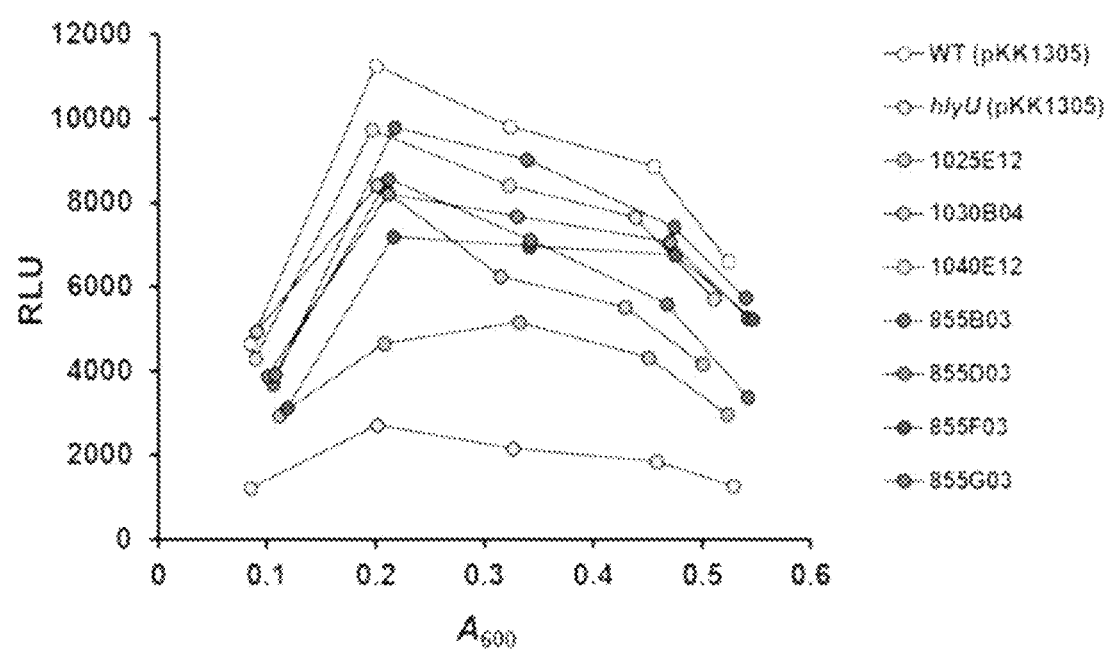
FIG. 4 shows the results of verification of HlyU inhibitory activity of 1025E12 (hereinafter referred to as "CM2660"), 1030B04, 1040E12, 855B03, 855D03, 855F03 and 855G03 using wild-type Vibrio vulnificus introduced with the lux reporter plasmid (pKK1305), lux expression of which is activated by HlyU, and hlyU-mutant Vibrio vulnificus introduced with the lux reporter plasmid (pKK1305), lux expression of which is activated by HlyU.

For the experiments, the pZK1608 plasmid having the promoter directly inhibited by HlyU and the pKK1305 plasmid having the promoter activated by HlyU were introduced via conjugation into wild-type and hlyU mutant strains (hlyU-knocked out strains) of *Vibrio vulnificus*. The constructed wild-type *Vibrio* reporter strain was treated with sample compounds and cultured at 30° C., and cell growth and luminescence were measured in the same manner as the *E. coli* strain screening (FIG. 3 and FIG. 4). FIG. 3 shows the results of verification of HlyU inhibitory activity of 1025E12 (hereinafter referred to as "CM2660"), 1030B04, 1040E12, 855B03, 855D03, 855F03 and 855G03 using wild-type *Vibrio vulnificus* introduced with the lux reporter plasmid (pZW1608), lux expression of which is repressed by HlyU, and hlyU-mutant *Vibrio vulnificus* introduced with the lux reporter plasmid (pZW1608), lux expression of which is repressed by HlyU. FIG. 4 shows the results of verification of HlyU inhibitory activity of 1025E12 (hereinafter referred to as "CM2660"), 1030B04, 1040E12, 855B03, 855D03, 855F03 and 855G03 using wild-type *Vibrio vulnificus* introduced with the lux reporter plasmid (pKK1305), lux expression of which is activated by HlyU, and hlyU-mutant *Vibrio vulnificus* introduced with the lux reporter plasmid (pKK1305), lux expression of which is activated by HlyU.

When the wild-type *Vibrio vulnificus* containing the pZW1608 plasmid was treated with DMSO, as a control group, HlyU was not inhibited by DMSO, and lux operon was inhibited by HlyU, so that light was not increased, but was maintained at a low level. However, when treated with inhibitor compounds, HlyU was inhibited, lux operon was activated, and light was increased to a relatively high level compared to the case of DMSO treatment, to emit light (FIG. 3).

Meanwhile, when wild-type *Vibrio vulnificus* containing pKK1305 plasmid was treated with DMSO, HlyU was not inhibited and lux operon was activated by HlyU, so that light gradually increased and decreased as the cells grew, which forms an inverted U-shaped graph. However, when wild-type *Vibrio vulnificus* having pKK1305 plasmid was treated with the inhibitor compounds, HlyU was inhibited and lux operon was not activated by HlyU, so that the luminescence level was decreased (FIG. 4).

From the above results, it could be seen that the compounds of the present invention are not only *E. coli* reporter strains, but also inhibitors suppressing HlyU activity in *Vibrio vulnificus*.

Meanwhile, among the compounds noted above, the compound 1025E12 having the best effect was selected as a HlyU inhibitor, was referred to as "CM2660", and was used in the following experiment. CM2660 having the structure of Formula 1 is N-(4-oxo-4H-thieno[3,4-c]chromen-3-yl)-3-phenylprop-2-ynamide) of the present invention.

EXAMPLE 2

Identification of the Effect of "Compound I Group"

Figure 5:
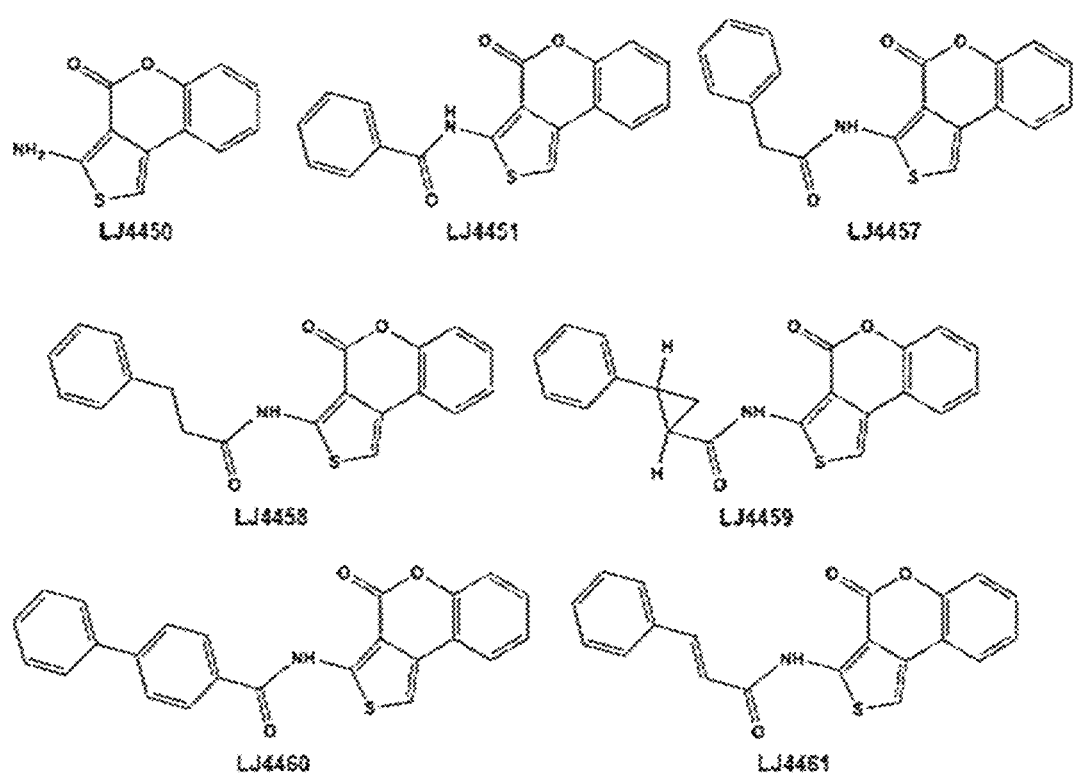
FIG. 5 shows the chemical structure of Compound Group I.

In order to identify whether or not a specific structure of CM2660 has a significant effect on HlyU inhibition, the effect of HlyU inhibition by the compound CM2660 and derivatives thereof, "Compound Group I" (FIG. 5) was verified. For the purpose, the pKK1305 plasmid prepared in Example 1 was conjugated to the wild-type *Vibrio vulnificus*, and the *Vibrio* reporter strain (pKK1305 in wild-type *V. vulnificus*) thus produced was treated with various concentrations of the derivative compounds. FIG. 5 shows the chemical structure of Compound Group I.

Figure 6:
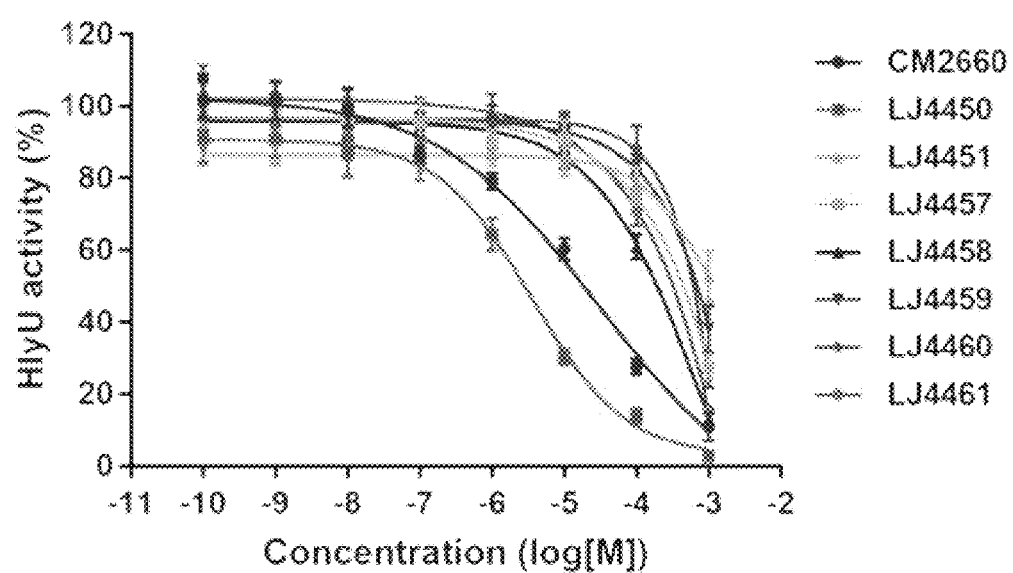
FIG. 6 shows the result of verification of the inhibitory ability against HlyU activity of Compound Group I.

While culturing at 30° C., the growth of the reporter strain and the degree of bioluminescence thereof were measured in the same manner as in Example 1, and the RLU was calculated. The RLU of the DMSO-treated control group was expressed as 100% HlyU activity. HlyU activity was plotted according to the concentration of the derivative compound, and $EC_{50}$ (half maximal effective concentration) was calculated using GraphPad Prism 7.0 (GraphPad Software, San Diego, Calif.) (FIG. 6, Table 2). FIG. 6 shows the result of verification of the inhibitory ability against HlyU activity of Compound Group I.

TABLE 2

| Compound | $EC_{50}$ (µM) |
| --- | --- |
| CM2660 (Formula 11) | 30.94 |
| LJ4450 | 3.53 |
| LJ4451 (Formula 12) | 993 |
| LJ4457 (Formula 13) | $1018 \times 10^6$ |
| LJ4458 (Formula 14) | 874.6 |
| LJ4459 (Formula 15) | $29.67 \times 10^6$ |
| LJ4460 (Formula 16) | $0.3953 \times 10^6$ |
| LJ4461 (Formula 17) | $73.7 \times 10^6$ |

As a result, the scaffold of CM2660, LJ4450, showed the lowest $EC_{50}$ value and the highest HlyU inhibitory effect. However, LJ4450 inhibited the growth of *Vibrio vulnificus* and was thus excluded from further experiments because of the possibility of occurrence of resistance. CM2660 exhibited an $EC_{50}$ value of 30.94 µM and other derivative compounds also showed a HlyU inhibitory effect, although weaker than that of CM2660. This result is considered to be because the triple bond of CM2660 plays a key role in HlyU inhibition. Overall, it was expected that derivative compounds having structural similarity to CM2660 will inhibit the expression of virulence factors of *Vibrio vulnificus* by inhibiting HlyU.

EXAMPLE 3

Identification of Effect of Compound Group II

Figure 7:
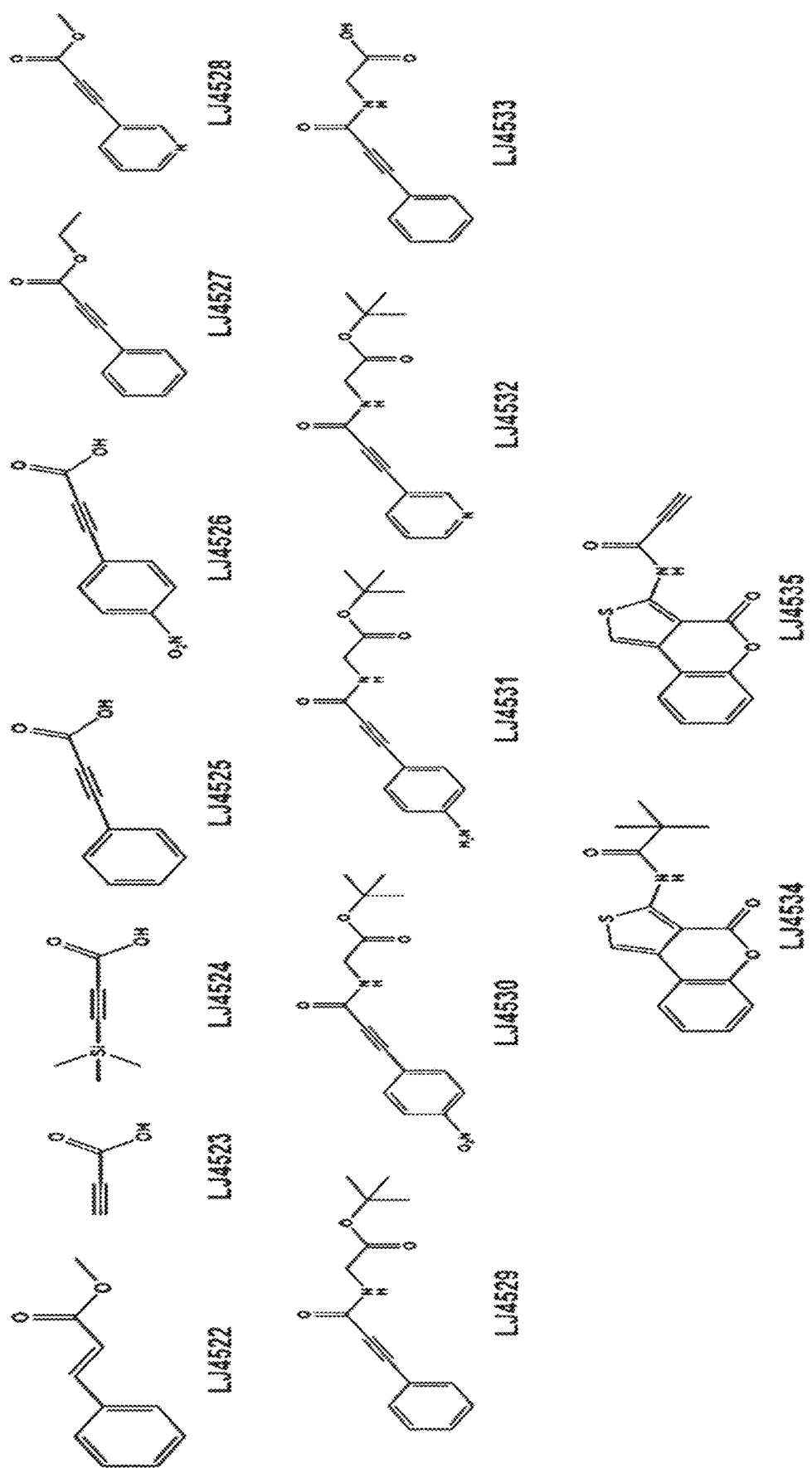
FIG. 7 shows the chemical structure of Compound Group II.

Meanwhile, in order to identify whether or not the triple bond of CM2660 has a significant effect on HlyU inhibition, the HlyU inhibitory effect by "Compound Group II", the derivative of compound CM2660, was verified (FIG. 7). FIG. 7 shows the chemical structure of Compound Group II.

Figure 8:
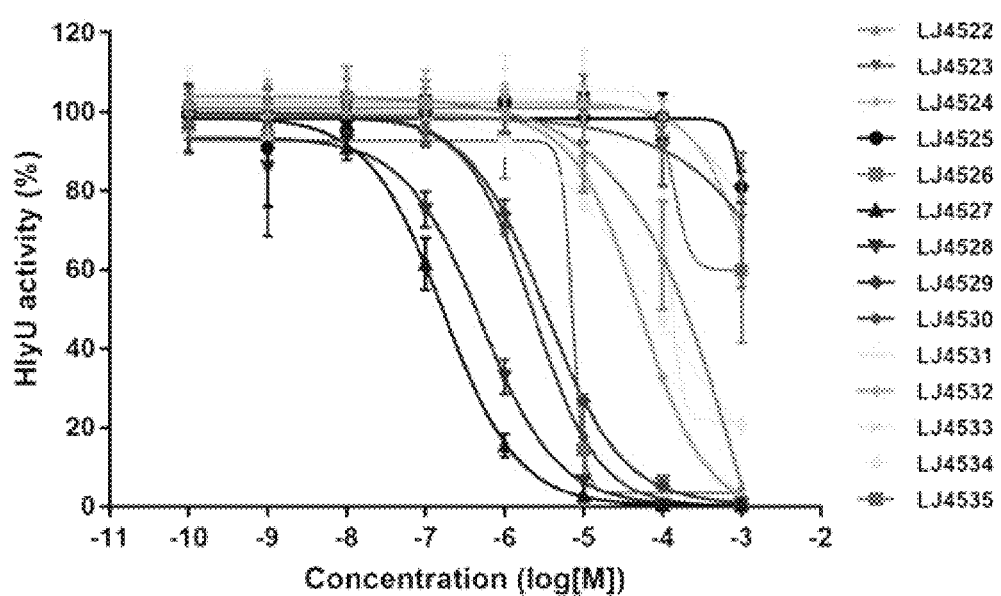
FIG. 8 shows the result of verification of the inhibitory ability against HlyU activity by Compound Group II.

For this purpose, $EC_{50}$ values were calculated using the same experimental method as in Example 2 (FIG. 8, Table 3). FIG. 7 shows the chemical structure of the compound group II and FIG. 8 shows the result of verification of the inhibitory ability against HlyU activity by the Compound Group II.

TABLE 3

| Compound | EC$_{50}$ (μM) |
| --- | --- |
| LJ4522 (Formula 21) | 1,790 |
| LJ4523 (Formula 22) | $6.17 \times 10^6$ |
| LJ4524 (Formula 23) | 1,380 |
| LJ4525 (Formula 24) | 1,310 |
| LJ4526 (Formula 25) | 140 |
| LJ4527 | 0.17 |
| LJ4528 | 0.5 |
| LJ4529 | 3.26 |
| LJ4530 | 2.29 |
| LJ4531 (Formula 26) | 118 |
| LJ4532 (Formula 27) | 52.36 |
| LJ4533 (Formula 28) | 1,140 |
| LJ4534 (Formula 29) | 71.6 |
| LJ4535 | 7.31 |

The experimental result showed that, among the 14 derivative compounds, referred to as "LJ4522 to LJ4535", five compounds, namely, LJ4527, LJ4528, LJ4529, LJ4530 and LJ4535, showed lower EC$_{50}$ values than CM2660. However, these compounds inhibited the growth of *Vibrio vulnificus* and thus were excluded from further experiments. Overall, it was expected that derivative compounds having structural similarity to CM2660 will inhibit the expression of virulence factors of *Vibrio vulnificus* by inhibiting HlyU.

Experimental Example 1

Identification of Mechanism of Action of CM2660 and Derivatives Thereof

In order to identify whether the compounds selected in Examples 1 to 3 can control the virulence of pathogenic microorganisms with low possibility of causing antibiotic resistance without directly killing *Vibrio* bacteria, the following experiment was conducted to identify the mechanism of action of CM2660 and derivatives thereof. However, when the mechanism of action of CM2660 is identified, the mechanism of action of derivatives thereof, that is, LJ4451, LJ4457, LJ4458, LJ4459, LJ4460, LJ4461, LJ4522, LJ4523, LJ4524, LJ4525, LJ4526, LJ4531, LJ4532, LJ4533 and LJ4534, can be deduced. In the following experiments, the description of only CM2660 represents description of effects of derivatives thereof.

Figure 9:
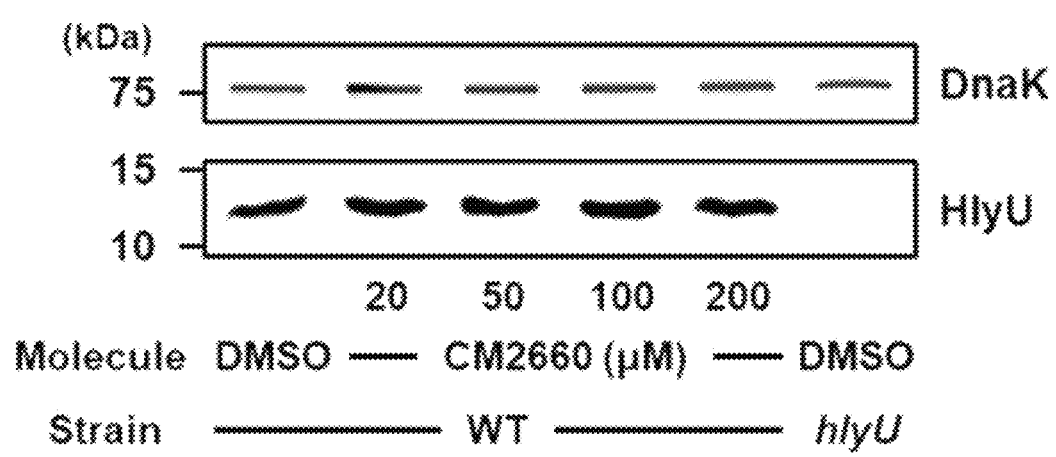
FIG. 9 shows the result of determination of the amount of HlyU protein in the cells of Vibrio vulnificus upon treatment of the cells with CM2660.

(1) Identification Whether Compound CM2660 Directly Inhibits HlyU Activity Rather Than Decreasing Intracellular Concentration of HlyU In order to determine the mechanism by which the HlyU inhibitor CM2660 inhibited the activity of HlyU, *Vibrio vulnificus* was cultured at 30° C. and treated with various concentrations of CM2660 at A$_{600}$=0.2. *Vibrio vulnificus* was treated with 2% DMSO as a control group. Then, the cell solution was centrifuged at A$_{600}$=0.5, indicating the time when the intracellular amount of HlyU was maximized, and only the cell portion (pellet) was recovered. The recovered cells were chemically lysed to determine the amount of HlyU in each sample (FIG. 9). FIG. 9 shows the result of determination of the amount of HlyU protein in the cells of *Vibrio vulnificus* upon treatment of the cells with CM2660. When treating with CM2660 at a concentration within the experimental range, the amount of HlyU in each sample showed no significant difference. This indicates that CM2660 directly inhibits HlyU activity, rather than controlling the intracellular expression level of HlyU.

Figure 10:
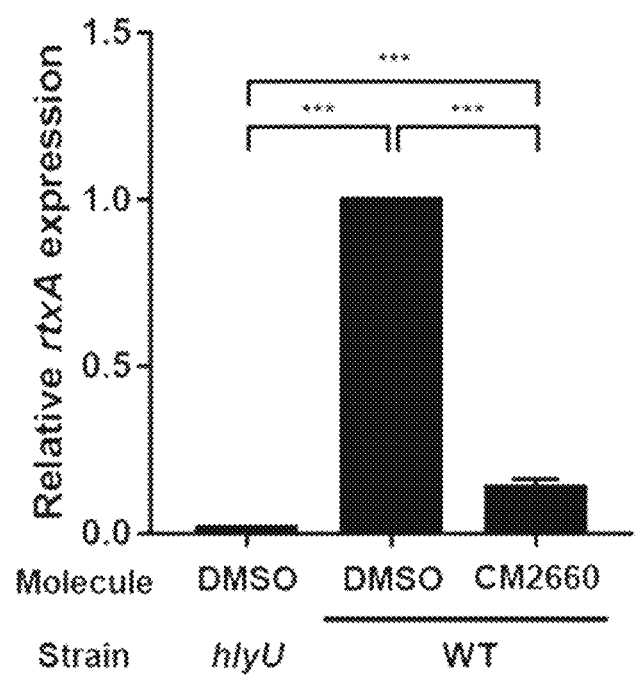
FIG. 10 shows the result of determination of the level of rtxA mRNA at $A_{600}$=0.5 when treating Vibrio vulnificus with 20 μM CM2660.
Figure 11:
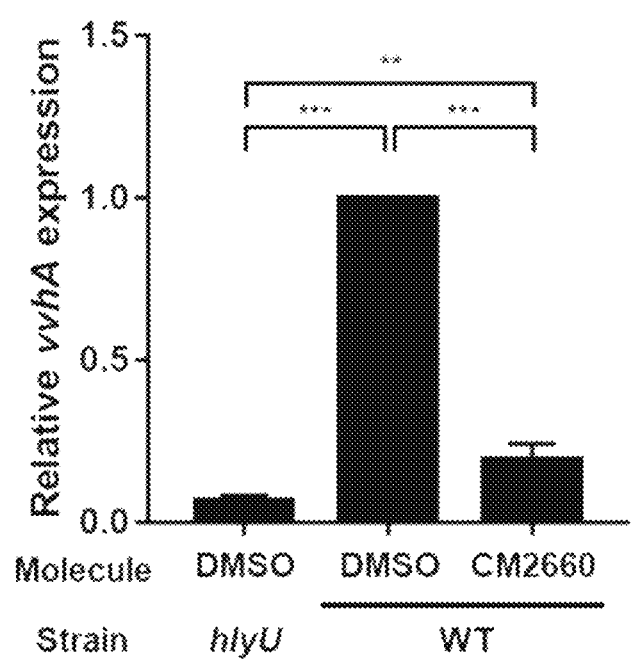
FIG. 11 shows the result of determination of the level of vvhA mRNA at $A_{600}$=0.5 when treating Vibrio vulnificus with 20 μM CM2660.
Figure 12:
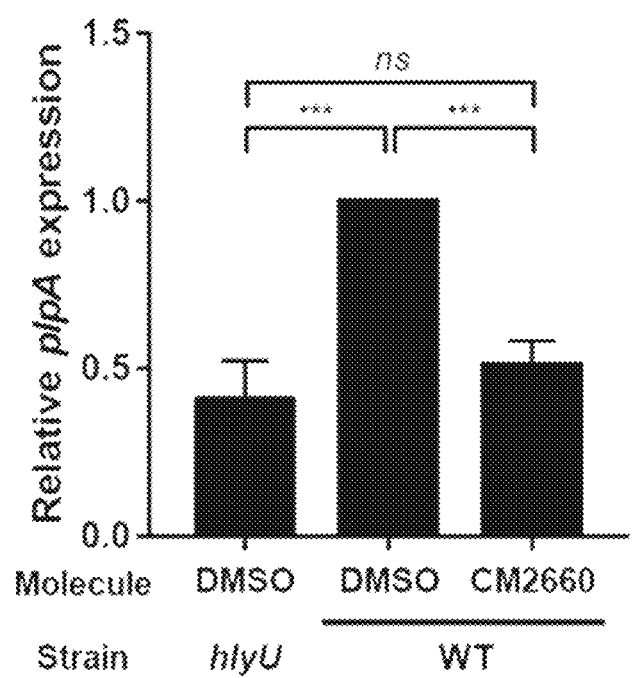
FIG. 12 shows the result of determination of the level of plpA mRNA at $A_{600}$=1.0 when treating Vibrio vulnificus with 20 μM CM2660.

(2) Identification Whether or Not Compound CM2660 Inhibits Expression of rtxA, vvhA and plpA Genes Activated by HlyU The effect of CM2660 on the expression of rtxA, vvhA and plpA, the virulence genes of *Vibrio vulnificus* activated by HlyU, was investigated. For this purpose, *Vibrio vulnificus* were first cultured at 30° C., and was treated with CM2660 at a final concentration of 20 μM at A$_{600}$=0.2. *Vibrio vulnificus* were treated with 2% DMSO as a control group. Then, the culture solution were sampled at the time at which the expression of each gene was mainly controlled by HlyU (A$_{600}$=0.5 for rtxA and vvhA, and A$_{600}$=1.0 for plpA), RNA was purified, and quantitative real-time polymerase chain reaction (quantitative Real-Time (qRT)-PCR) was performed (FIGS. 10 to 12). FIG. 10 shows the result of determination of the level of rtxA mRNA at A$_{600}$=0.5 when treating *Vibrio vulnificus* with 20 μM CM2660, FIG. 11 shows the result of determination of the level of vvhA mRNA at A$_{600}$=0.5 when treating *Vibrio vulnificus* with 20 μM CM2660, and FIG. 12 shows the result of determination of the level of plpA mRNA at A$_{600}$=1.0 when treating *Vibrio vulnificus* with 20 μM CM2660. The results showed that the expression of the virulence genes rtxA, vvhA and plpA of *Vibrio vulnificus* activated by HlyU was significantly reduced by the compound CM2660.

(3) Identification Whether Compound CM2660 Decreases Virulence of *Vibrio vulnificus* In Vitro Whether or not the reduction of the expression of the virulence genes, rtxA, vvhA, and plpA by the compound CM2660 leads to a reduction in the virulence of *Vibrio vulnificus* was identified. The effects of CM2660 on the virulence of *Vibrio vulnificus* were investigated using human epithelial cells, INT-407 cells and human erythrocytes.

Figure 13:
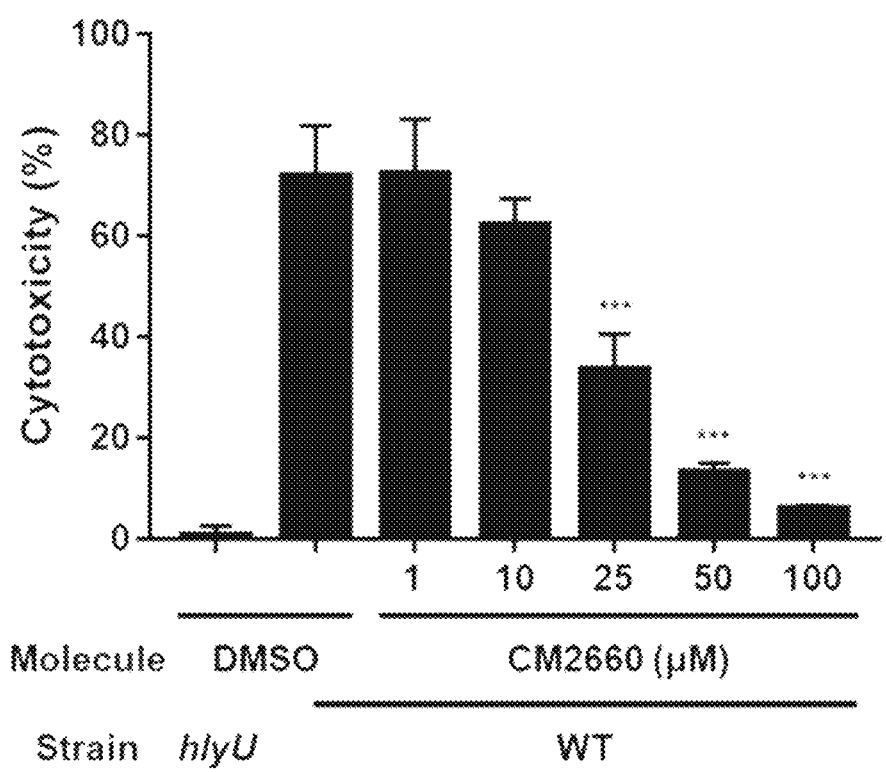
FIG. 13 shows the result of determination of the occurrence of cytotoxicity when treating Vibrio vulnificus with CM2660 at different concentrations.

*Vibrio vulnificus* cultured to A$_{600}$=0.5 at 30° C. was treated with various concentrations of CM2660 or DMSO (control group) and infected into INT-407 cells prepared in 96-well assay plates at multiplicity of infection (MOI) of 10 for 2.5 hours. Then, the 96-well assay plates were centrifuged to separate INT-407 cells, and the supernatant and the lactate dehydrogenase (LDH) activity in the supernatant was measured to determine the occurrence of virulence (FIG. 13). FIG. 13 shows the result of determination of the occurrence of cytotoxicity when treating *Vibrio vulnificus* with CM2660 at different concentrations. The treatment with CM2660 resulted in a concentration-dependent decrease in the virulence occurrence of *Vibrio vulnificus*.

Meanwhile, the effect of CM2660 on the hemolytic activity against erythrocytes of *Vibrio vulnificus* was investigated. For this purpose, *Vibrio vulnificus* was cultured at 30° C. and treated with CM2660 at different concentrations at A$_{600}$=0.2. *Vibrio vulnificus* was treated with 2% DMSO, as a control group, and each culture solution was cultured to A$_{600}$=1.0 and centrifuged to recover the supernatant. The filtered supernatant was concentrated and mixed with erythrocytes diluted to 10% in PBS and cultured at 37° C. Hemolytic activity against erythrocytes was quantified by measuring absorbance at 540 nm (A$_{540}$). A sample completely dissolved by treatment with 5% Triton X-100 instead of the supernatant was used as a positive control group and a sample using LBS medium was used as a negative control group.

Figure 14:
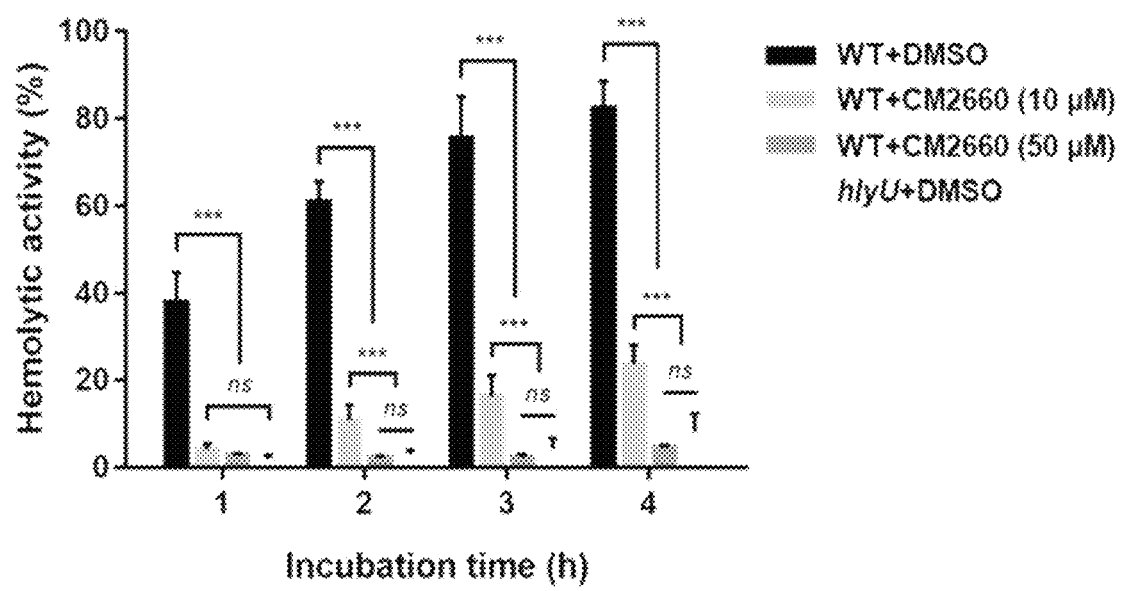
FIG. 14 shows the result of verification of the hemolytic activity against erythrocytes by treating Vibrio vulnificus with CM2660 at different concentrations.

Hemolytic activity was calculated using the following Equation 2, and is shown as a percentage (%) in FIG. 14.

$$\frac{\text{Absorbance of sample} - \text{absorbance of negative control group}}{\text{Absorbance of positive control group} - \text{absorbance of negative control group}} \quad \text{[Equation 2]}$$

FIG. 14 shows the result of verification of the hemolytic activity against erythrocytes by treating *Vibrio vulnificus* with CM2660 at different concentrations. In the same behavior as the reduction of toxicity, CM2660 treatment resulted in a concentration-dependent decrease in hemolytic activity against erythrocytes of *Vibrio vulnificus*.

Overall, it was confirmed that the compound CM2660 decreased the virulence of *Vibrio vulnificus* in vitro in a concentration dependent manner.

(4) Identification Whether Or Not Compound CM2660 Inhibits Binding of HlyU to DNA In order to investigate the effect of CM2660 on the DNA-binding capability of the HlyU protein, electrophoretic mobility shift assay (EMSA) experiments were performed using DNA at the known HlyU-binding rtxA promoter site.

The promoter site of the rtxA gene was amplified by PCR using $^{32}$P-labeled primer, PrtxA-R (5'-ACTAGTTAT-TTTTTTGATCCTGGCCTAC-3') and unlabeled primer PrtxA-F (5'-GAGCTCGAATCAAATAAAATGGC-3'). This DNA probe was reacted with 50 nM or 100 nM HlyU, 100 μM CM2660 or DMSO in reaction buffer (10 mM Tris-Cl, 50 mM KCl, 5 mM MgCl$_2$, 0.75 mM DTT and 5% glycerol, 0.1 μg poly(dl-dC)) at 25° C. for 30 minutes.

Figure 15:
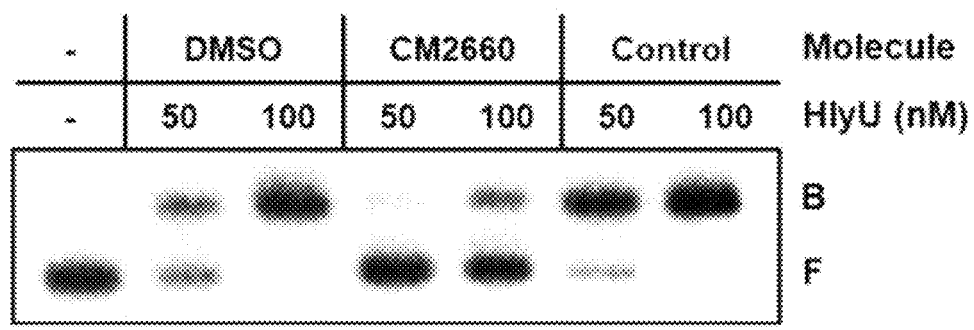
FIG. 15 shows the result of determination of the DNA-binding capability of HlyU when treated with DMSO, CM2660 and the control compound (the compound randomly selected from compounds which did not exhibit HlyU inhibitory activity, among about 8,400 compounds screened in Example 1)
Figure 16:
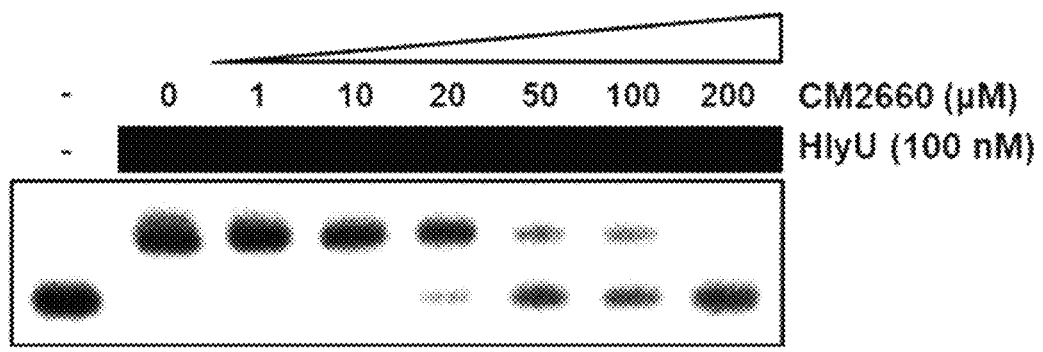
FIG. 16 shows the result of determination of DNA-binding capability of HlyU when treated with CM2660 at different concentrations.

The DNA-HlyU complex was electrophoresed on a polyacrylamide gel and phosphoimaged through Typhoon FLA7000 to determine the band position (FIG. 15, FIG. 16). FIG. 15 shows the result of determination of the DNA-binding capability of HlyU when treated with DMSO, CM2660 and the control compound (the compound randomly selected from compounds which did not exhibit HlyU inhibitory activity, among about 8,400 compounds screened in Example 1) and FIG. 16 shows the result of determination of DNA-binding capability of HlyU when treated with CM2660 at different concentrations. When treated with DMSO or the control group, the DNA-binding capability of HlyU did not change, but when treated with CM2660, the binding capability was significantly decreased. This decrease became greater as the concentration of CM2660 increased.

(5) Investigation on HlyU Inhibition Mechanism of Compound CM2660

Figure 17:
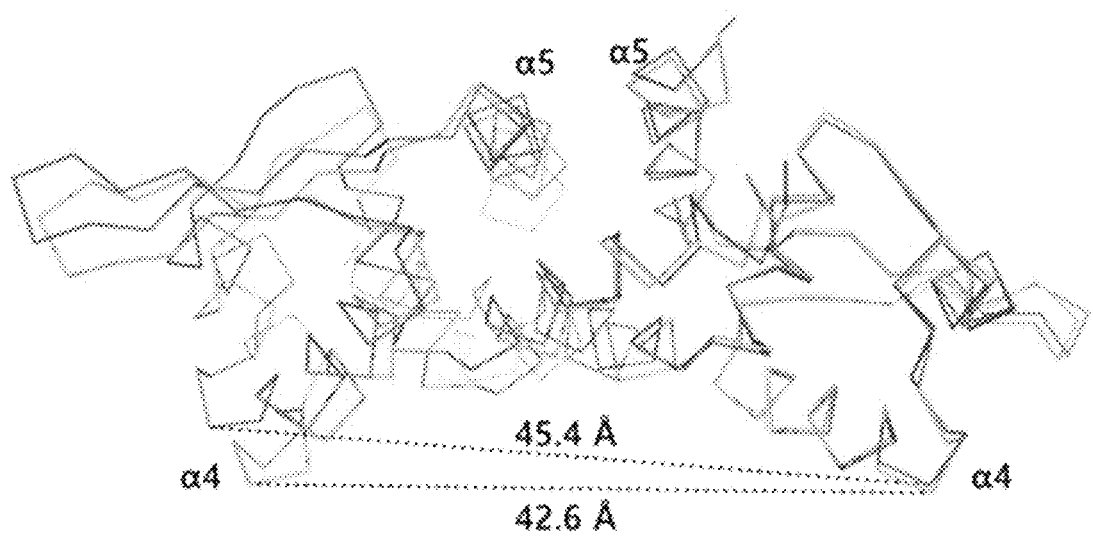
FIG. 17 shows the result of a comparison between the structure of HlyU treated with CM2660 (green) and native HlyU (magenta, PDB code: 3JTH) non treated therewith.
Figure 18:
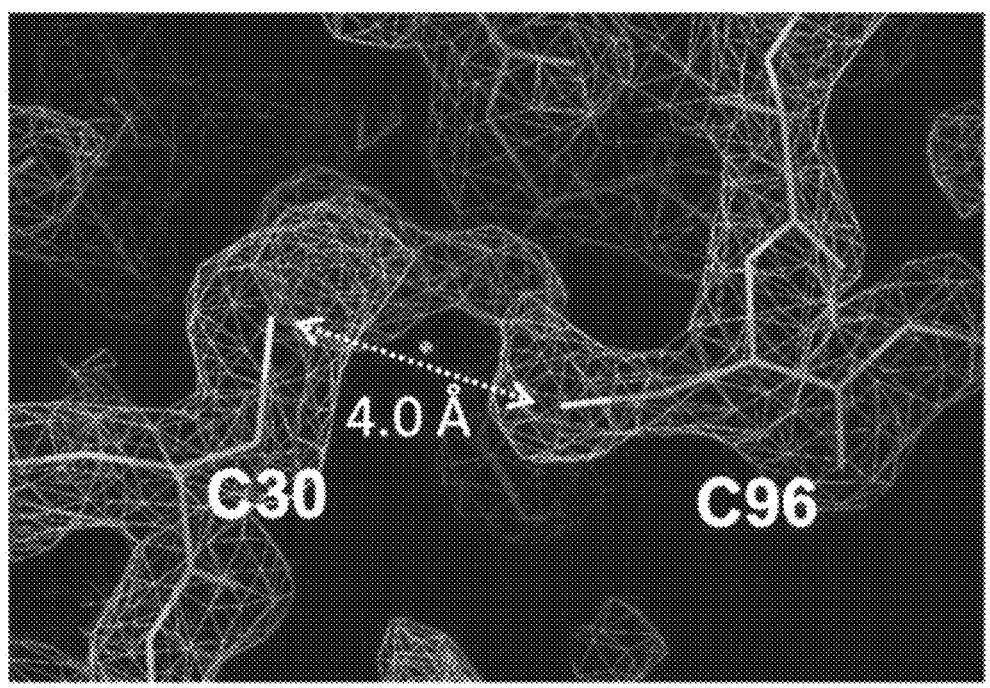
FIG. 18 shows electron density maps around Cys30 and Cys96 of the HlyU structure treated with CM2660 (a 2FoFc map outlined at $1.0\sigma$ is represented by a blue mesh and a 2FoFc map outlined at $3.0\sigma$ is represented by an aqua mesh)

In order to more accurately identify the HlyU inhibition mechanism of CM2660, the crystal structure of CM2660-treated HlyU protein was detected by X-ray crystallography and compared with that of the HlyU protein not treated with CM2660 (FIG. 17, FIG. 18). FIG. 17 shows the result of comparison between the structure of HlyU treated with CM2660 (green) and native HlyU (magenta, PDB code: 3JTH) not treated therewith, and FIG. 18 shows electron density maps around Cys30 and Cys96 of the HlyU structure treated with CM2660 (a 2FoFc map outlined at 1.0σ is represented by a blue mesh and a 2FoFc map outlined at 3.0σ is represented by an aqua mesh).

Figure 19:
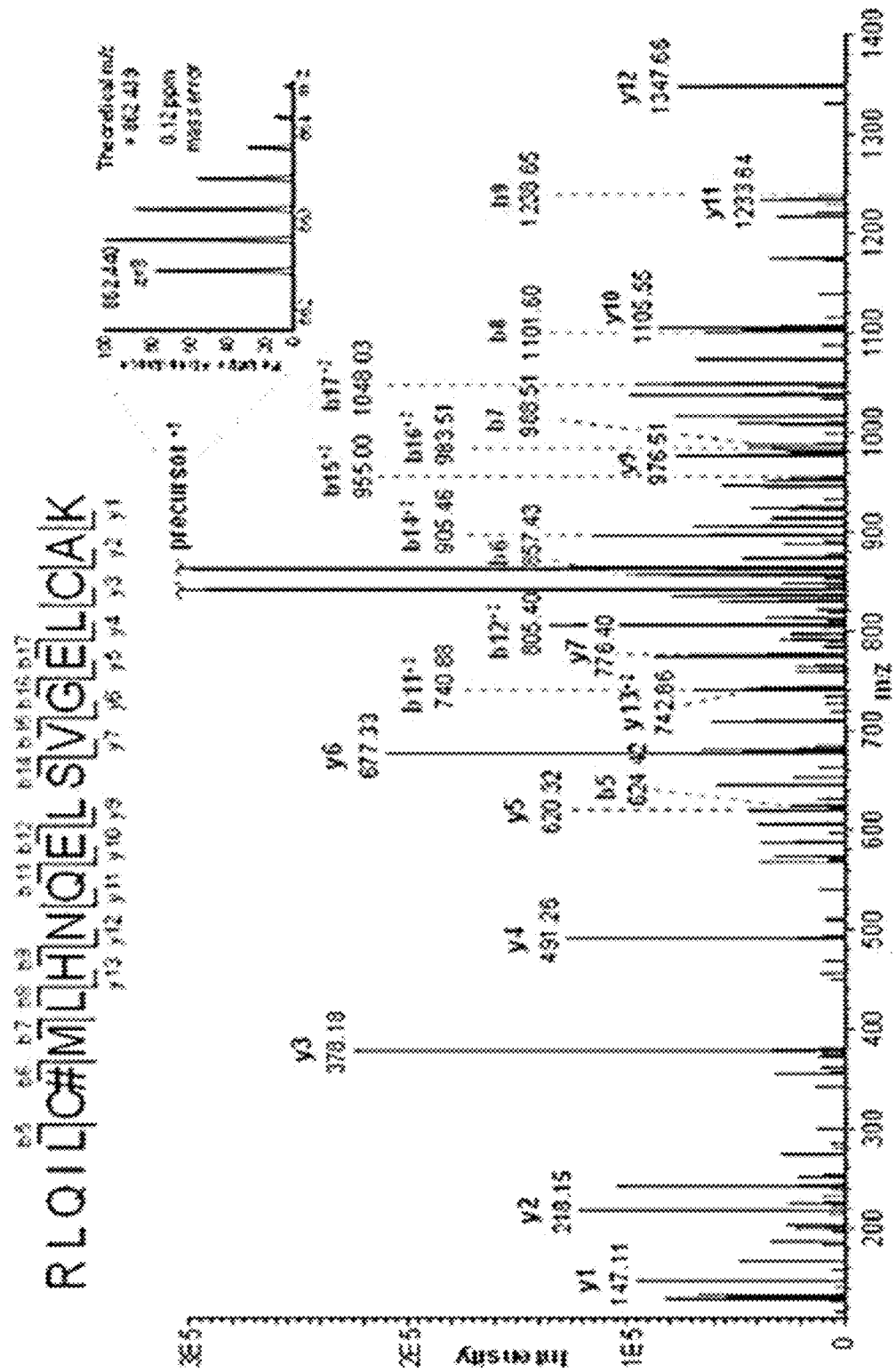
FIG. 19 shows the result of mass spectrometry analysis of HlyU protein samples treated with CM2660.

In order to identify this in more detail, samples of HlyU protein treated with CM2660 were analyzed using mass spectrometry. The result showed that cysteine residue at position 30 of the HlyU protein was covalently bound to a fragment of CM2660. In addition, the results of mass spectrometry analysis showed that the molecular weight of the CM2660 fragment corresponded to the increased molecular weight of the HlyU protein treated with CM2660 (FIG. 19). FIG. 19 shows the result of mass spectrometry analysis of HlyU protein samples treated with CM2660.

From the results, it was expected that CM2660 covalently bonded to the cysteine residue at position 30 of the HlyU protein mediated the structural change of the HlyU protein, resulting in reduction of the DNA-binding capability of the HlyU.

(6) Investigation of Effect of Compound CM2660 on Growth of *Vibrio vulnificus*

Figure 20:
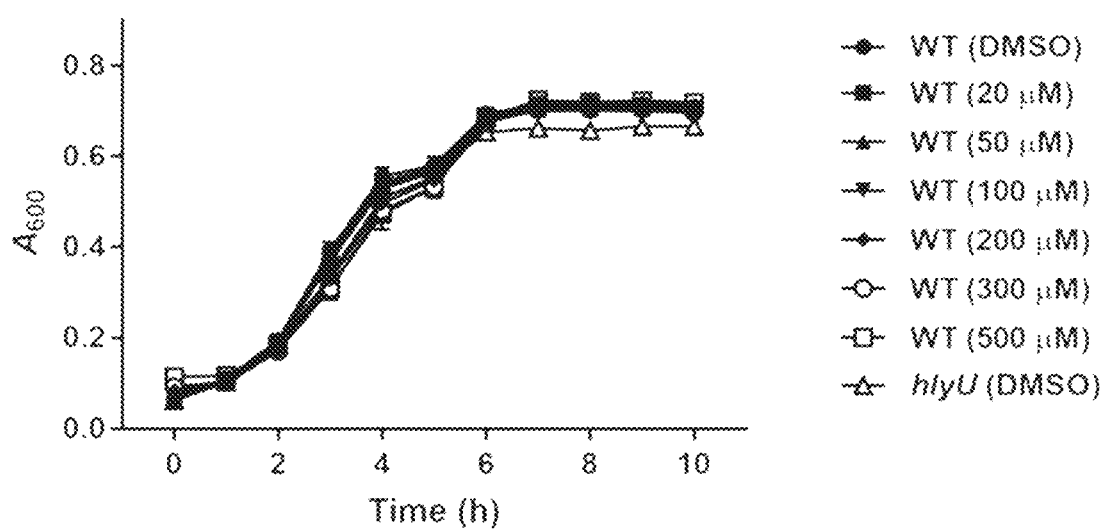
FIG. 20 shows the result of determination of the effect of CM2660 on the growth of *Vibrio vulnificus*.
Figure 21:
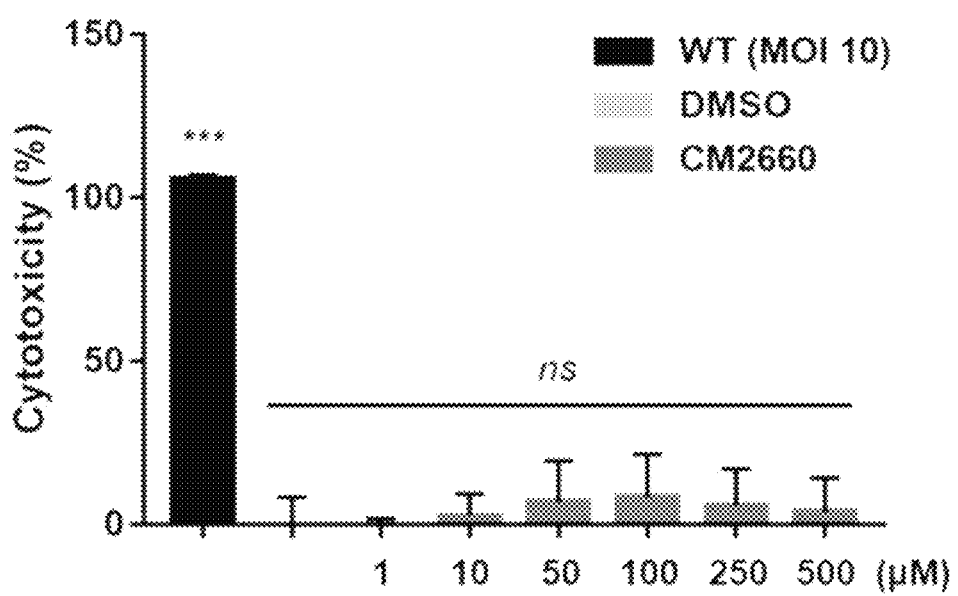
FIG. 21 shows the result of determination of the toxicity of CM2660 in human epithelial cells, that is, INT-407 cells.

When CM2660 inhibits the growth of *Vibrio vulnificus*, it is likely to induce resistance, as in the case of conventional antibiotics that directly inhibit growth. Therefore, *Vibrio vulnificus* was treated with various concentrations of CM2660, and the growth of *Vibrio vulnificus* was observed (FIG. 20). FIG. 20 shows the results of determination of the effect of CM2660 on the growth of *Vibrio vulnificus*.

Treatment with 20-500 μM CM2660 had no significant effect on in-vitro growth of *Vibrio vulnificus*.

Figure 22:
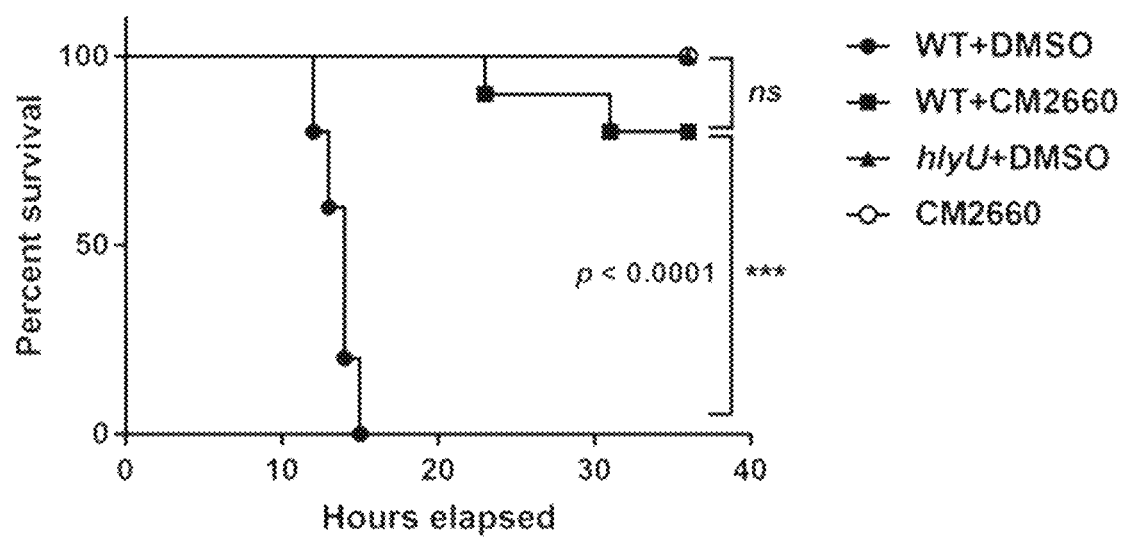
FIG. 22 is a graph showing the result of observation of the expression of in-vivo toxicity of *Vibrio vulnificus* after injecting CM2660 into mice.
Figure 23:
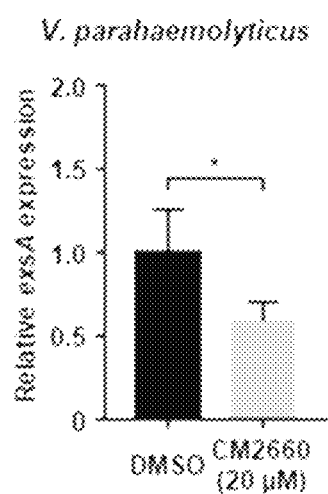
FIG. 23 shows the result of determination of the mRNA level of exsA at $A_{600}=0.5$ upon treatment of *Vibrio parahaemolyticus* with 20 µM CM2660.
Figure 24:
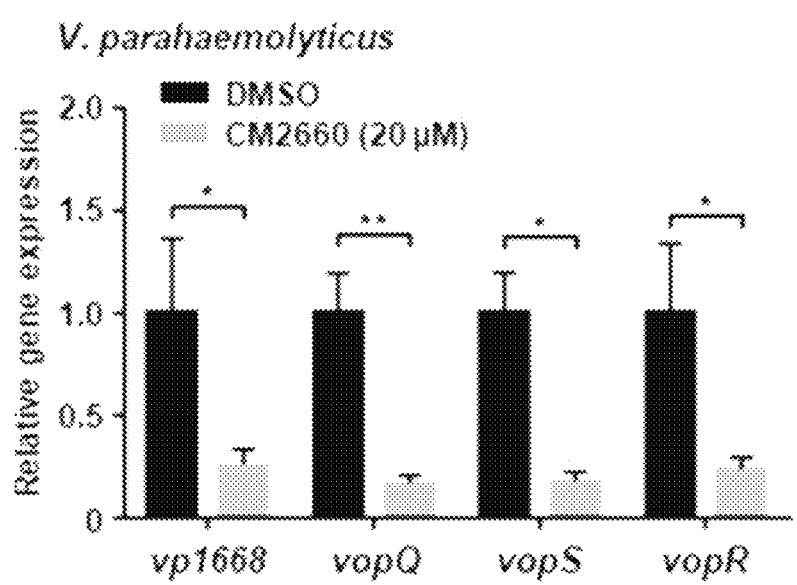
FIG. 24 shows the results of determination of the mRNA levels of vp1668, vopQ, vopS and vopR at $A_{600}=0.5$ when treating *Vibrio parahaemolyticus* with 20 µM CM2660.
Figure 25:
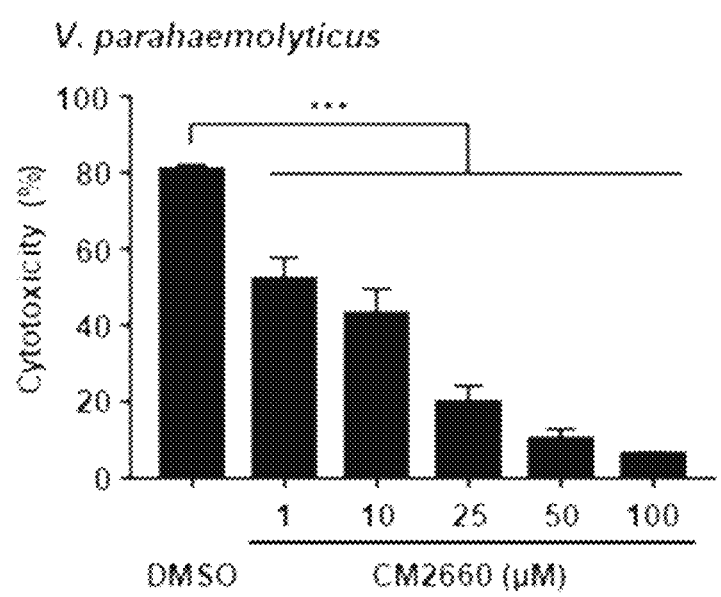
FIG. 25 shows the result of determination of the occurrence of cytotoxicity by treating *Vibrio parahaemolyticus* with CM2660 at different concentrations.
Figure 27:
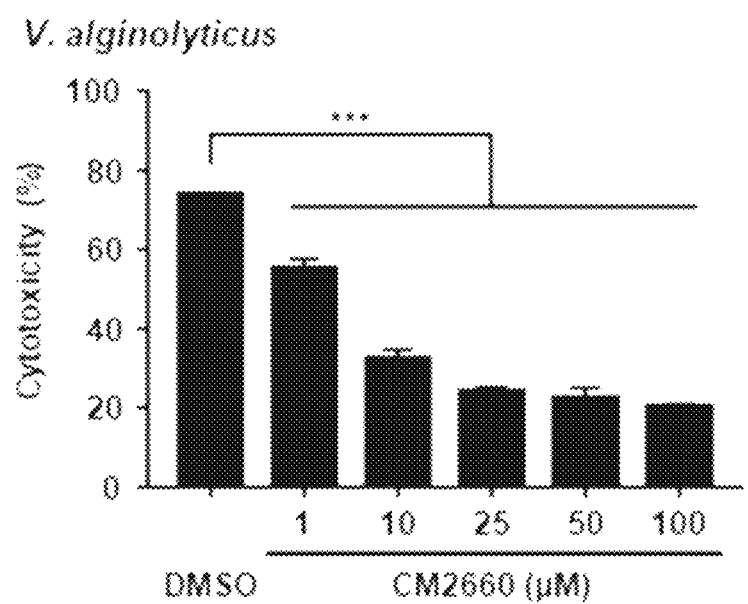
FIG. 27 shows the result of determination of cytotoxicity when treating *Vibrio alginolyticus* with CM2660 at different concentrations.
Figure 28:
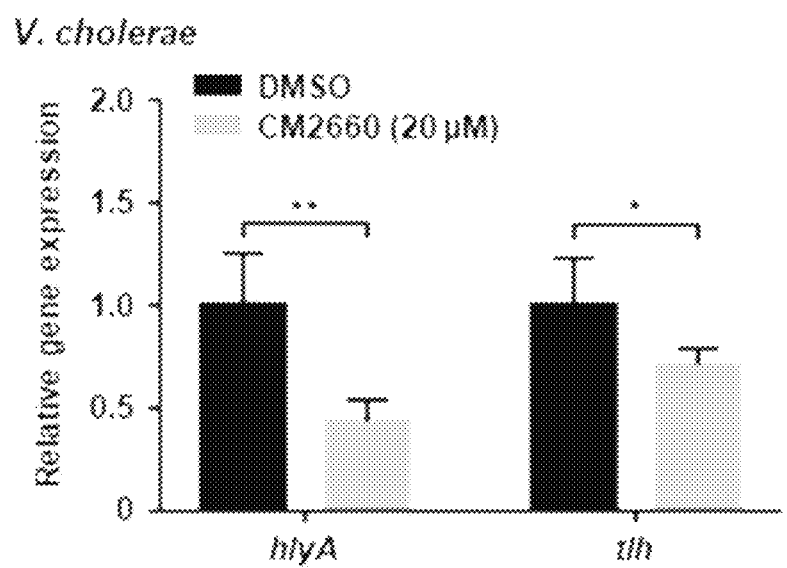
FIG. 28 shows the result of determination of the mRNA levels of hlyA and tlh at $A_{600}=0.5$ when treating *Vibrio cholerae* with 20 µM CM2660.
Figure 29:
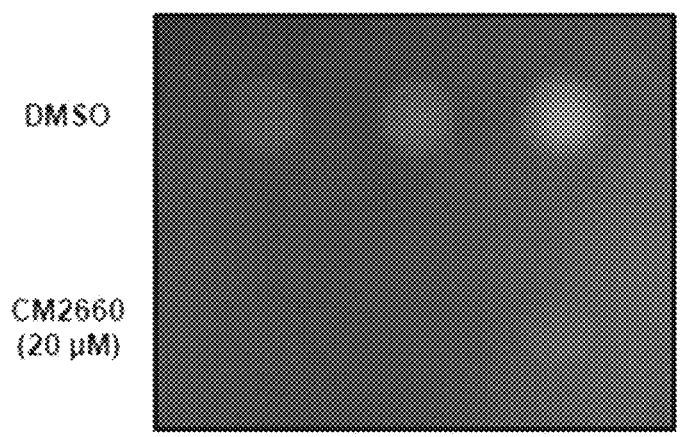
FIG. 29 shows the result of determination of hemolytic activity when treating *Vibrio cholerae* with 20 µM CM2660.

These results indicate that CM2660 of the present invention decreases virulence without inhibiting the growth of *Vibrio vulnificus*. This also means that CM2660 controls the pathogenic microorganisms by a mechanism different from conventional antibiotics that try to remove the corresponding pathogenic factors from the host by killing the pathogenic microorganisms. That is, this shows that the virulence of the pathogenic microorganisms can be controlled with a low possibility of causing antibiotic resistance, and that control of pathogenic microorganisms exhibiting resistance is possible through the method of the present invention.

(7) Investigation of Cytotoxicity of Compound CM2660

In order to investigate the in-vitro cytotoxicity of CM2660, human epithelial cells, INT-407 cells were treated with *Vibrio vulnificus* (control) of MOI 10, and 1 to 500 μM of CM2660 or DMSO. After 3 hours, LDH release assay was performed and cytotoxicity was measured (FIG. 21). FIG. 21 shows the result of determination of the toxicity of CM2660 in human epithelial cells, that is, INT-407 cells. Cytotoxicity (%) was calculated with respect to the cytotoxicity obtained through treatment of 5% Triton-X 100 as 100%. CM2660 showed almost no cytotoxicity to INT-407 cells in all concentration ranges (1 to 500 μM), similar to the cytotoxicity of the solvent, DMSO. This suggests that the compound CM2660 had no cytotoxicity.

(8) Identification Whether Compound CM2660 Decreases In-Vivo Toxicity of *Vibrio vulnificus*

In order to determine whether or not CM2660 also decreases the virulence of *Vibrio vulnificus* in vivo using 7-week-old ICR female mice, *Vibrio vulnificus* cultured at $A_{600}$=0.5 at 30° C. was prepared. This was mixed with DMSO (10%) or CM2660 (1.4 mg/kg of mouse body weight) and the resulting mixture was subcutaneously injected into the back of mice anesthetized with isoflurane. In addition, only CM2660 was injected subcutaneously in order to determine the in-vivo toxicity of CM2660 (FIG.

22). FIG. 22 is a graph showing the results of observation of the expression of in-vivo toxicity of *Vibrio vulnificus* after injecting CM2660 into mice.

Mice infected with *Vibrio vulnificus* treated with CM2660 showed significantly higher viability (survival) than the control group (DMSO). This means that CM2660 attenuated the toxicity of *Vibrio vulnificus* even in vivo. In addition, the fact that all mice subcutaneously injected with CM2660 alone survived indicated that CM2660 did not show in-vivo toxicity.

Experimental Example 2

Identification Whether Compound CM2660 Decreases Toxicity of Other *Vibrio vulnificus*

In addition to *Vibrio vulnificus*, *Vibrio* species include *V. parahaemolyticus*, *V. cholerae*, *V. alginolyticus*, etc., which are pathogenic in humans and shellfish. Whether or not CM2660 attenuated toxicity by inhibiting HlyU of other *Vibrio* species, since these *Vibrio* species also have the HlyU protein, was investigated.

(1) Investigation of Effect of Compound CM2660 on *V. parahaemolyticus*

In *V. parahaemolyticus*, HlyU is known to activate the gene expression of the master transcriptional regulator, exsA of type III secretion system-1 (T3SS-1), which causes cytotoxicity. In order to determine whether or not CM2660 reduces the expression of the exsA gene by inhibiting HlyU of *V. parahaemolyticus*, virulence gene expression of *V. parahaemolyticus* was investigated using the same method as in (2) of Experimental Example 1.

In order to induce the T3SS-1 gene expression of *Vibrio* parahaemolyticus, *Vibrio parahaemolyticus* was cultured in Dulbecco's Modified Eagle Medium (DMEM) medium. *Vibrio parahaemolyticus* was treated with CM2660 at a final concentration of 20 μM at $A_{600}$=0.2 and was treated with 2% DMSO as a control group. After 3 hours, the culture solution was sampled and RNA was purified to perform qRT-PCR (FIG. 23). As a result of the experiment, it was found that the expression of exsA, the virulence gene of *Vibrio parahaemolyticus* activated by HlyU was significantly decreased. FIG. 23 shows the result of determination of the mRNA level of exsA at $A_{600}$=0.5 upon treatment of *Vibrio parahaemolyticus* with 20 μM CM2660.

Meanwhile, since ExsA activates the expression of the T3SS-1 gene of *Vibrio parahaemolyticus*, T3SS-1 gene expression was detected using the same sample to determine whether or not the expression of exsA leads to a decrease in T3SS-1 gene expression (FIG. 24). The test result showed that the expression of vp1668, vopQ, vopS and vopR, which are the T3SS-1 genes of *Vibrio parahaemolyticus*, all decreased significantly when treated with CM2660. FIG. 24 shows the results of determination of the mRNA levels of vp1668, vopQ, vopS and vopR at $A_{600}$=0.5 when treating *Vibrio parahaemolyticus* with 20 μM CM2660.

Furthermore, as can be seen from FIG. 25, the decrease in the expression of these T3SS-1 genes leads to a decrease in the cytotoxicity of *Vibrio parahaemolyticus* using the method (3) of Experimental Example 1. FIG. 25 shows the result of determination of the occurrence of cytotoxicity by treating *Vibrio parahaemolyticus* with CM2660 at different concentrations.

(2) Identification of Effect of Compound CM2660 on *Vibrio alginolyticus*

*Vibrio alginolyticus* is also a pathogenic *Vibrio* bacterium that has T3SS and is cytotoxic, similar to *Vibrio parahaemolyticus*. In order to determine the toxin inhibition effect of CM2660 in *Vibrio* alginolyticus, *Vibrio alginolyticus* was cultured in TSB (tryptic soy broth) medium supplemented with 1% NaCl. *Vibrio alginolyticus* was treated with CM2660 at a final concentration of 20 μM at $A_{600}$=0.2, was treated with 2% DMSO as a control group, the culture solution was sampled at $A_{600}$=0.5, and the expression of T3SS virulence genes of *Vibrio alginolyticus* was determined in the same manner as above (FIG. 26).

The test result showed that CM2660 significantly reduced the expression of exsA of *Vibrio alginolyticus* and va11668, vopQ, vopS and vopR, which are T3SS genes. FIG. 26 shows the results of determination of mRNA levels of exsA, va11668, vopQ, vopS and vopR at $A_{600}$=0.5 when treating *Vibrio alginolyticus* with 20 μM CM2660.

In addition, it was found that the cytotoxicity of *Vibrio alginolyticus* was reduced in a concentration-dependent manner (FIG. 27). FIG. 27 shows the result of determination of cytotoxicity when treating *Vibrio alginolyticus* with CM2660 at different concentrations.

(3) Investigation of Effect of Compound CM2660 on *Vibrio* cholerae

In *Vibrio cholerae*, HlyU is known to directly activate the expression of the hemolytic protein, HlyA. In order to identify the effect of CM2660 on *Vibrio* cholerae, *Vibrio cholerae* was cultured in LB medium at 37° C., was treated with CM2660 at a final concentration of 20 μM at $A_{600}$=0.2 and was treated with 2% DMSO as a control group. The culture solution was sampled at $A_{600}$=0.5 and RNA was purified to perform qRT-PCR. As a result, CM2660 significantly reduced the expression of hlyA, the hemolytic protein gene of *Vibrio cholerae*. In addition, the expression of the other hemolytic protein tlh gene, which was translocated and transcribed with the hlyA gene, was also significantly reduced (FIG. 28). FIG. 28 shows the result of determination of the mRNA levels of hlyA and tlh at $A_{600}$=0.5 when treating *Vibrio cholerae* with 20 μM CM2660.

Meanwhile, in order to determine whether or not the reduction in the expression of the hemolytic protein gene as described above leads to a decrease in the hemolytic activity of *Vibrio cholerae*, the supernatant of *Vibrio cholerae* was sampled in the same manner as in (3) of Experimental Example 1. *Vibrio cholerae* supernatant when treated with DMSO was dotted in horse blood agar medium and cultured at 37° C. for 24 hours. As a result, a clear zone produced by hemolysis of horse blood was observed. However, when treated with CM2660, the clear zone did not appear well, indicating that hemolytic activity of *Vibrio cholerae* was reduced by CM2660 (FIG. 29). FIG. 29 shows the result of determination of the hemolytic activity when treating *Vibrio cholerae* with 20 μM CM2660.

Overall, the results showed that CM2660 effectively reduced the virulence of *Vibrio* cholerae, *Vibrio* parahaemolyticus, *Vibrio alginolyticus* and *Vibrio vulnificus.*

REFERENCE

1. Jang, K. K., Lee, Z. W., Kim, B., Jung, Y. H., Han, H. J., Kim, M. H., Kim, B. S., and Choi, S. H. 2017. Identification and characterization of *Vibrio vulnificus* plpA encoding a phospholipase A₂ essential for pathogenesis. J. Biol. Chem. 292: 17129-17143.

2. Fullner, K. J., and Mekalanos, J. J. 1999. Genetic characterization for a new type IV-A pilus gene cluster found in both classical and El Tor biotypes of *Vibrio cholerae*. Infect. Immun. 67: 1393-1404.

3. Lenz, D. H., Mok, K. C., Lilley, B. N., Kulkarni, R. V., Wingreen, N. S., and Bassler, B. L. 2004. The small RNA chaperone Hfq and multiple small RNAs control quorum sensing in *Vibrio harveyi* and *Vibrio cholerae*. Cell. 118: 69-82.

4. Guzman, L. M., Belin, D., Carson, M. J., and Beckwith, J. 1995. Tight regulation, modulation, and high-level expression by vectors containing the arabinose PBAD promoter. J. Bacteriol. 177:4121-4130.

The invention claimed is:

1. A method for alleviating or treating *Vibrio* infection comprising administering to a subject in need thereof an effective amount of N-(4-oxo-4H-thieno[3,4-c]chromen-3-yl)-3-phenylprop-2-ynamide having the structure of Formula 11, or a derivative thereof selected from the group consisting of the compound having the structure of the following Formula 12, Formula 13, Formula 14, Formula 15, Formula 16, Formula 17, and Formula 29:

[Formula 11]

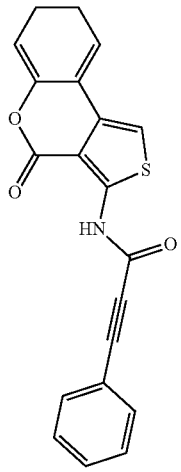

[Formula 12]

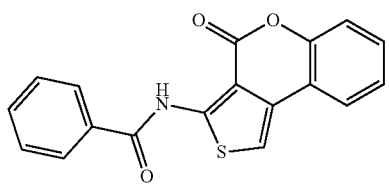

[Formula 13]

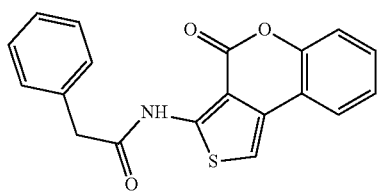

[Formula 14]

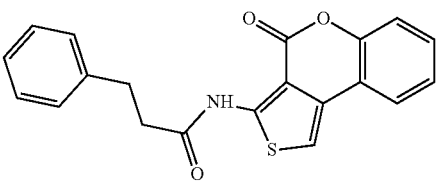

[Formula 15]

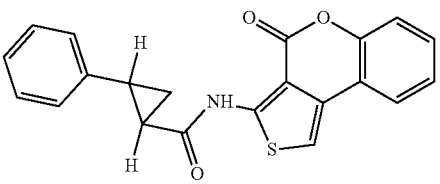

[Formula 16]

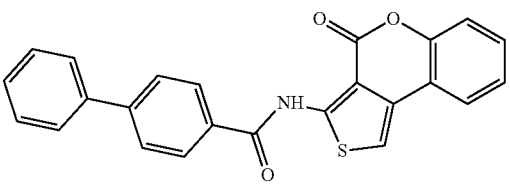

[Formula 17]

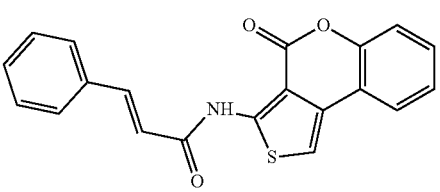

[Formula 29]

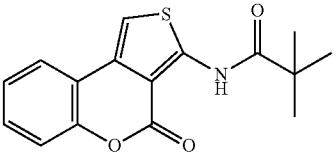

2. The method of claim 1, wherein N-(4-oxo-4H-thieno[3,4-c]chromen-3-yl)-3-phenylprop-2-ynamide or the derivative thereof inhibits activity of HlyU by covalently binding to the transcriptional regulator protein HlyU, which activates expression of (a) rtxA, which is an RTX toxin gene of *Vibrio* bacteria, (b) vvhA, which is a hemolysin gene thereof, and (c) plpA, which is a phospholipase gene thereof.

3. The method of claim 1, wherein the *Vibrio* bacteria comprises any one selected from *Vibrio* cholerae, *Vibrio* parahaemolyticus, *Vibrio vulnificus* and *Vibrio* alginolyticus.

* * * * *